(12) United States Patent
Stefanovic et al.

(10) Patent No.: US 11,548,874 B2
(45) Date of Patent: Jan. 10, 2023

(54) ANTIFIBROTIC COMPOUNDS AND RELATED METHODS

(71) Applicants: Florida State University Research Foundation, Inc., Tallahassee, FL (US); The Florida International University Board of Trustees, Miami, FL (US)

(72) Inventors: Branko Stefanovic, Tallahassee, FL (US); Adel Nefzi, Port Saint Lucie, FL (US)

(73) Assignees: Florida State University Research Foundation, Inc., Tallahassee, FL (US); The Florida International University Board Of Trustees, Miami, FL (US)

( * ) Notice: Subject to any disclaimer, the term of this patent is extended or adjusted under 35 U.S.C. 154(b) by 37 days.

(21) Appl. No.: 17/319,812

(22) Filed: May 13, 2021

(65) Prior Publication Data
US 2021/0363131 A1    Nov. 25, 2021

Related U.S. Application Data

(60) Provisional application No. 63/107,705, filed on Oct. 30, 2020, provisional application No. 63/026,933, filed on May 19, 2020.

(51) Int. Cl.
| | | |
|---|---|---|
| *C07D 401/14* | (2006.01) | |
| *C07D 403/14* | (2006.01) | |
| *A61K 31/506* | (2006.01) | |
| *A61P 43/00* | (2006.01) | |
| *C07D 403/04* | (2006.01) | |
| *A61P 17/02* | (2006.01) | |

(52) U.S. Cl.
CPC ............ *C07D 403/04* (2013.01); *A61P 17/02* (2018.01)

(58) Field of Classification Search
CPC .. C07D 401/14; C07D 403/14; A61K 31/506; A61P 43/00
See application file for complete search history.

(56) References Cited

U.S. PATENT DOCUMENTS

| | | | | |
|---|---|---|---|---|
| 7,943,628 B2* | 5/2011 | Bell | ........................ | A61P 31/12 544/323 |
| 8,404,652 B2 | 3/2013 | Higashi | | |
| 8,889,677 B2* | 11/2014 | Grauert | ................ | C07D 403/12 514/253.09 |
| 9,006,450 B2* | 4/2015 | Roth | ........................ | A61P 3/00 546/290 |
| 10,654,834 B2* | 5/2020 | Huang | ...................... | A61P 3/10 |
| 2012/0009151 A1* | 1/2012 | Han | ........................ | A61P 31/00 435/375 |
| 2017/0327503 A1 | 11/2017 | Glad et al. | | |

OTHER PUBLICATIONS

Borthwick et al., *Mycobacterium tuberculosis* Decaprenylphosphoryl-.beta.-D-ribose, Oxidase Inhibitors: Expeditious Reconstruction of Suboptimal Hits into a Series with Potent in Vivo Activity, Journal of Medicinal Chemistry, vol. 63, No. 5, pp. 2557-2576 (Year: 2020).*
International Search Report dated Sep. 14, 2021 for PCT/US2021/032187.
Life Chemicals; "SID 318890128"; PubChem, Chemical Vendors; Nov. 11, 2016.

* cited by examiner

*Primary Examiner* — Brenda L Coleman
(74) *Attorney, Agent, or Firm* — Christopher M. Ramsey; GrayRobinson, P.A.

(57) ABSTRACT

This discloses that compounds of Formula 1 have antifibrotic properties. In particular, this discloses a pharmaceutical composition including one or more compounds of Formula 1 and methods of using compounds of Formula 1 in fibrosis treatment and inhibiting type 1 collagen synthesis.

53 Claims, 22 Drawing Sheets

ANTIFIBROTIC COMPOUNDS AND RELATED METHODS

CROSS-REFERENCE TO RELATED APPLICATIONS

This claims the benefit of priority from U.S. Application No. 63/026,933, filed May 19, 2020, and U.S. Application No. 63/107,705, filed Oct. 30, 2020. The entire contents of these prior applications are incorporated by reference.

FIELD

This relates to the field of inhibiting type 1 collagen synthesis and, more particularly, to compounds that inhibit collagen synthesis.

BACKGROUND

Fibrosis is a chronic disease characterized by excessive synthesis and deposition of type 1 collagen into the extracellular matrix of various organs. Because treating fibrosis may require many years of treatment, antifibrotic drugs are preferably highly specific and substantially nontoxic. For this reason, there are very few FDA-approved antifibrotic drugs.

BRIEF SUMMARY

In view of the foregoing, what is needed is new compounds that can be used to treat fibrotic conditions.

An example of antifibrotic composition includes a pharmaceutical dosage form including a compound of the formula

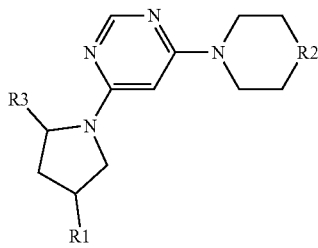

and/or a pharmaceutically effective salt thereof.

In this formula, R1 may be selected from a halogen, a hydrogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group.

In this formula, R2 maintains the six-membered ring and is selected from:
(i) an amide group, a thioamide group, a valeramide group, a myristic amide group, a benzamide group, a carboxylamide group, and a phenylacetamide group;
(ii) O, S, CR4R5 where R4 and R5 are independently selected from a hydrogen, a halogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group; or
(iii) N—R2' where R2' is selected from a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, and a thiourea group.

In this formula, R3 may be selected from:
(i) a halogen, a hydrogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group; or
(ii) OH, OR6, NH$_2$, and NHR6R7 where R6 is selected from H, an aliphatic group, an alkylaryl group, a cycloalkyl group, an alkylcycloalkyl group, and an aryl group; R7 and R8 are independently selected from H, an aliphatic group, an alkylaryl group, a cycloalkyl group, an alkylcycloalkyl group, and an aryl group.

This composition may further include one or more of the following features.

R1 may be selected from 3-methylvaleramide, myristic amide, 2,4-diclhlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide.

R2 may be selected from 3,4-dicholorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide.

R3 may be an amide group.

R1 may be selected from 3-methylvaleramide, myristic amide, 2,4-diclhlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide; R2 may be selected from 3,4-dicholorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide; and R3 may be an amide group.

The pharmaceutical dosage form may be at least one of a pill or an injectable dosage form.

Formula 1 may be substantially non-toxic.

An example of a method of treatment includes administering to a patient having a fibrotic condition a therapeutically amount of the composition to the patient. This method may further include one or more of the following features.

R1 may be selected from 3-methylvaleramide, myristic amide, 2,4-diclhlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide.

R2 may be selected from 3,4-dicholorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide.

R3 may be an amide group.

R1 may be selected from 3-methylvaleramide, myristic amide, 2,4-diclhlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenylacetamide, and phenylacetamide; R2 may be selected from 3,4-dicholorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide; and R3 may be an amide group.

The fibrotic condition may be at least one of a pulmonary fibrosis, a liver fibrosis, a heart fibrosis, a circulatory system fibrosis, a skin fibrosis, and an intestinal fibrosis.

Administering may be achieved by oral administration and/or administration by injection.

The pharmaceutical dosage form may be at least one of a pill or an injectable dosage form.

An example of a method of inhibiting collagen production includes contacting a cell capable of producing type 1 collagen with the composition, the composition being effective for inhibiting collagen production. This method may further include one or more of the following features.

R1 may be selected from 3-methylvaleramide, myristic amide, 2,4-diclhlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenylacetamide, and phenylacetamide.

R2 may be selected from 3,4-dicholorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide.

R3 may be an amide group.

R1 may be selected from 3-methylvaleramide, myristic amide, 2,4-diclhlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenylacetamide, and phenylacetamide. R2 may be selected from 3,4-dicholorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide; and R3 may be an amide group.

DETAILED DESCRIPTION OF EXAMPLE EMBODIMENTS

Figure 1:
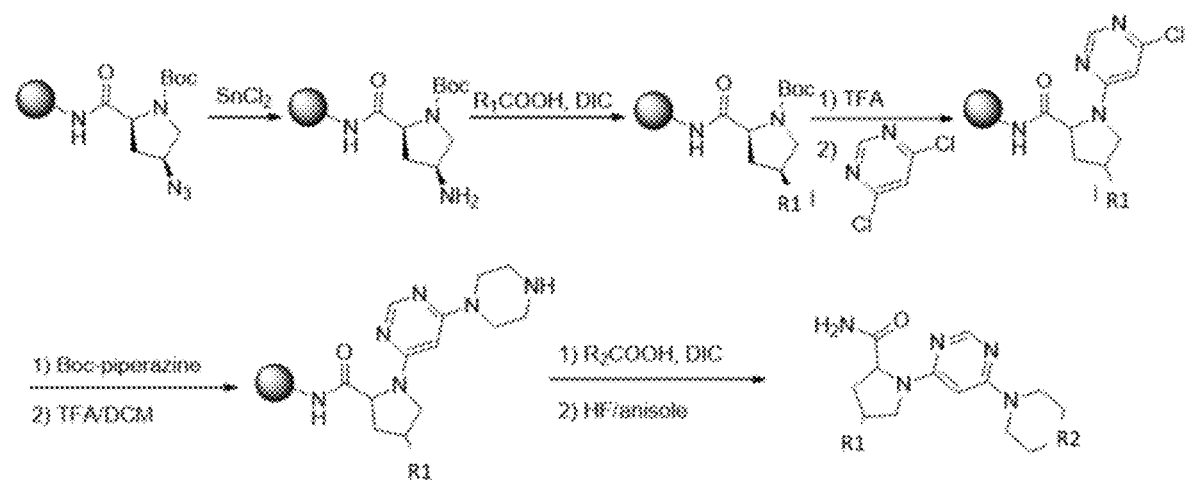
FIG. 1 is an example of a reaction scheme for making compounds of Formula 1.

This disclosure describes exemplary embodiments, but not all possible embodiments of the compositions and methods. Where a particular feature is disclosed in the context of a particular example, that feature can also be used, to the extent possible, in combination with and/or in the context of other examples. The compositions and methods may be embodied in many different forms and should not be construed as limited to only the examples described here.

An example of an antifibrotic compound includes Formula 1

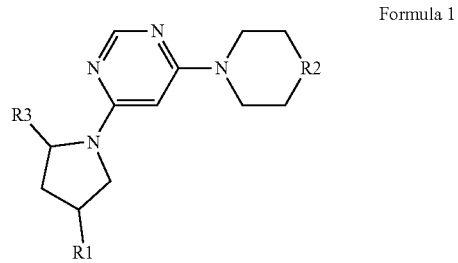

Formula 1 or a pharmaceutically acceptable salt thereof.

The compounds of Formula 1 may have stereoisomers. The compounds may include any isomer of Formula 1 or mixtures of such isomers. Some compounds of Formula 1 have one or more asymmetric carbon atoms and may be obtained as a racemic mixture of stereoisomers that can be resolved.

The compounds of Formula 1 may have tautomers, meaning they may exist as two or more chemical compounds that are capable of interconversion. This often means the exchange of a hydrogen atom between two other atoms. Tautomers exist in equilibrium with each other, thus attempts to prepare the separate forms usually results in the formation of a tautomer mixture.

Compounds of Formula 1 that are basic may form pharmaceutically acceptable salts with inorganic acids such as hydrohalic acids such as hydrochloric acid and hydrobromic acid, sulphuric acid, nitric acid and phosphoric acid, and the like, and with organic acids such as acetic acid, tartaric acid, succinic acid, fumaric acid, maleic acid, malic acid, salicylic acid, citric acid, methanesulphonic acid and p-toluene sulphonic acid, and the like. The formation and isolation of such salts can be carried out according to conventional methods for forming and isolating pharmaceutically acceptable salts.

In certain examples of Formula 1, R1 may be selected from a halogen, a hydrogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group.

In certain examples of Formula 1, R1 may be selected from 3-methylvaleramide, myristic amide, 2,4-diclhlorobenzamide, 2-(P-Toluoyl)-benzamide, 1-methyl-2-pyrrolecarboxylamide, 4-isobutyl-alpha-methylphenyacetamide, 4-bromobenzamide, pentafluorophenyacetamide, and phenylacetamide.

In certain examples of Formula 1, R2 may be selected so that it maintains the six-membered ring.

In certain examples of Formula 1, R2 may be selected from O, S, CR4R5 where R4 and R5 are independently selected from a hydrogen, a halogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group.

In certain examples of Formula 1, R2 may be selected from N—R2' where R2' is selected from a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, and a thiourea group.

In certain examples of Formula 1, R2 may be selected from an amide group, a thioamide group, a valeramide group, a myristic amide group, a benzamide group, a carboxylamide group, a phenylacetamide group, 3,4-dicholorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide.

In certain examples of Formula 1, R3 may be selected from a halogen, a hydrogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group.

In certain examples of Formula 1, R3 may be selected from OH, OR6, $NH_2$, NHR7R8. R6 may be selected from selected from H, an aliphatic group, an alkylaryl group, a cycloalkyl group, an alkylcycloalkyl group, and an aryl group. R7 and R8 may be independently selected from H, an aliphatic group, an alkylaryl group, a cycloalkyl group, an alkylcycloalkyl group, and an aryl group.

An alkyl group may be a straight, cyclic, or branched chain alkane hydrocarbon residue containing 1 to 12 carbon atoms. In certain examples, the alkyl group may be a straight or branched chain hydrocarbon residue containing 1 to 7 carbon atoms. Examples of particular alkyl groups include methyl, ethyl, propyl, isopropyl, n-butyl, isobutyl, and tert-butyl. The alkyl group may be substituted with substituents.

In certain examples, an aryl group may be a substituted phenyl or napthyl. Aryl groups may include examples such as benzyl, tolyl, xylyl, and the like. Suitable substituents for aryl may be, for example, alkyl, halogen, hydroxy, and optionally substituted alkyl, haloalkyl, alkenyl, alkynyl and aryloxy.

In certain examples, an alkoxy group may be optionally substituted straight or branched chain alkyl-oxy group where the alkyl portion is defined above. Examples may include methoxy, ethoxy, n-propyloxy, i-propyloxy, n-butyloxy, i-butyloxy, tert-butyloxy, pentyloxy, hexyloxy, and heptyloxy.

In certain examples a carbonyl group may be a group containing R—C=O optionally substituted with any of the other groups mentioned herein.

Any of the compounds of Formula 1 or any combination thereof may be administered as an active ingredient in a pharmaceutical dosage form composition. In such a case, the compounds of Formula 1 may be blended with one or more ingredients useful for making the composition into a pharmaceutically acceptable dosage form such as a suspension, tablet, capsule, injectable, dermal patch, or other dosage form.

Certain examples of the compounds of Formula 1 may be substantially non-toxic. Toxicity may be measured according to standard drug toxicity testing procedures. By being substantially non-toxic, the compound of Formula 1 may make a safer antifibrotic drug.

Exemplary ingredients include one or more excipients, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

The compound of Formula 1 is therapeutically effective for inhibiting type 1 collagen production. In some examples, the compound of Formula 1 is effective to inhibit binding of LARP6 with the 5' stem-loop of collagen mRNAs, thereby inhibiting collagen synthesis.

The pharmaceutical dosage form may include a combination of different antifibrotic drugs and may include one or more additional antifibrotic active ingredients that are therapeutically effective for treating a fibrotic condition.

The compound of Formula 1 used in the dosage form may be a pharmaceutically acceptable salt and/or derivative of a compound of Formula 1 such as any of the examples mentioned herein so long as the pharmaceutically acceptable salt and/or derivative is effective for inhibiting type 1 collagen synthesis.

The pharmaceutical composition may be administered as part of a dose regimen that includes varying changes in the dose during the treatment period.

There are many different ways that the compound of Formula 1 or the dosage form may be administered to the patient. These administration techniques include, but are not limited to administering one or more pharmaceutically acceptable dosage forms such as suspensions, tablets, suppositories, capsules, injectables, transdermals or the like. Other suitable administration techniques include oral, sublingual, buccal, intravenous, subcutaneous, transcutaneous, intramuscular, intracutaneous, intrathecal, epidural, intraocular, intracranial, inhalation, intranasal, or the like. Any combination of administration techniques may also be used.

An oral dosage form such as a pill includes a compound of Formula 1 combined with conventional excipients for tablet, capsule, or other pill-type dosage forms. The pill dosage form may be monolithic or particulate. Typical pill excipients may include binders such as sugars, gelatin, cellulose, starch, methyl cellulose, ethyl cellulose, hydroxypropyl methyl cellulose, and the like. They may also include fillers such as lactose, sucrose, cellulose, calcium carbonate, and the like. The pill may be formulated for extended or immediate release. If needed, the pill may be enteric coated.

An injectable dosage form may include the compound Formula 1 in a liquid carrier such as saline, oil, alcohol, or the like, optionally combined with a surfactant to aid solubility or emulsification of the compound Formula 1.

A method of inhibiting collagen production includes contacting a cell capable of producing type 1 collagen with the compound of Formula 1, the compound being effective for inhibiting collagen production.

In this method, the term "contacting" refers to placing the composition in direct physical association with the collagen producing cell. Contacting can be achieved using either a solid, liquid, or gaseous form of the effective compound. It includes events that take place both intracellularly and extracellularly. Contacting may also be accomplished by a conventional pharmaceutical administration technique that one would use on a patient. Suitable administration techniques include administering one or more pharmaceutically acceptable dosage forms such as suspensions, tablets, suppositories, capsules, injectables, transdermals or the like. Other suitable administration techniques include oral, sublingual, buccal, intravenous, subcutaneous, transcutaneous, intramuscular, intracutaneous, intrathecal, epidural, intraocular, intracranial, inhalation, itraperitoneal, or the like. Any combination of these administration techniques may also be used.

This method may also include any of the aforementioned features of the compound of Formula 1 and/or the pharmaceutical dosage form.

A method of treatment includes administering to a patient in need thereof a therapeutically effective amount of a compound of Formula 1 and/or the pharmaceutical dosage form to the patient.

Suitable administration techniques include any of the aforementioned administration techniques and associated pharmaceutical dosage forms.

The patient may be a human or animal subject that has been identified as having a fibrotic condition or is in need of antifibrotic treatment. Examples of fibrotic conditions include but are not limited to a pulmonary fibrosis, a liver fibrosis, a heart fibrosis, a circulatory system fibrosis, a skin fibrosis, a renal fibrosis and/or an intestinal fibrosis.

The therapeutically effective amount can vary and be adjusted to the patient's needs. By way of example, a daily dosage of between about 0.01 and about 100 mg/kg body weight per day should may be appropriate. A particular daily dosage range may be 0.1 to 500 mg/kg body weight, 0.1 to 250 mg/kg body weight, or 0.1 to 100 mg/kg body weight per day.

A typical dosage form may contain from about 5% w/w to about 95% w/w of the compound. A daily dose can be administered as a single dosage or in divided dosages as part of a dosing regimen.

If the composition includes a solution containing the compound of Formula 1, the concentration of the compound may be, for example, about 0.01 $\mu M$ to about 1,000 $\mu M$, about 1 $\mu M$ to about 500 $\mu M$, about 10 $\mu M$ to about 175 $\mu M$, about 10 $\mu M$ to about 150 $\mu M$, or about 10 $\mu M$ to about 125 $\mu M$, or about 10 $\mu M$ to about 100 $\mu M$, or about 10 $\mu M$ to about 25 $\mu M$.

Compounds of Formula 1 may be prepared by the procedure outlined FIG. 1 where R3, by way of example, is $NH_2-C=O$. A particular example of such a synthesis process is now described.

Starting from a p-methylbenzhydrylamine (MBHA) resin, pre-prepared Boc-L-Pro(4-N3)-OH (2S,4S) may be coupled in the presence of diisopropylcarbodiimide (DICI) and hydroxybenzotriazole (HOBt) in anhydrous dimethyl formamide (DMF) for about two hours. The azide group may be reduced in the presence of tin chloride ($SnCl_2$) in anhydrous DMF for 6-18 hours, and then treated with thiophenol and diisopropyllethylamine (DIEA) in DMF. The generated amine may be acylated with different commercially available R1-carboxylic acids in the presence of DICI in anhydrous DMF.

The Boc group may be cleaved in the presence of trifluoroacetic acid (TFA) in dichloromethane (DCM) (55:45) and the amine may be neutralized by washing the resin with a 5% solution of DIEA in DCM.

The free amine may be treated with 4,6-dichloropyrimidine in dioxane at 100° C. for about 24 hours. The second chloro group may be displaced by treatment of the resin with piperazine in dioxane while heating. The free amine of the piperazine ring may be acylated with a variety of commercially available R2-carboxylic acids in the presence of DIC.

The final desired compound may be released from the resin by conventional HF cleavage, and then extracted, lyophilized and purified by preparative HPLC. All the products may be confirmed by LC-MS and NMR analysis.

EXAMPLES

The following examples are provided to illustrate certain aspects of the composition and methods. These examples do not limit the scope of this disclosure or claims in any way.

Example 1: Synthesis of Compound 2659-17

This section provides an example of an antifibrotic compound that inhibits collagen production. This example is provided for illustration purposes and is not intended to limit the scope of what may be claimed.

Starting from a 100 mg sample of p-methylbenzhydrylamine (MBHA) resin, pre-prepared Boc-L-Pro(4-N3)-OH (2S,4S) (3 eq) was coupled in the presence of diisopropylcarbodiimide (DICI) (3 eq) and hydroxybenzotriazole (HOBt) (3 eq) in anhydrous dimethyl formamide (DMF) for two hours. The azide group was reduced in the presence of tin chloride ($SnCl_2$) in anhydrous DMF overnight, and then treated with thiophenol and diisopropyllethylamine (DIEA) in DMF. The generated amine was acylated with different commercially available carboxylic acids (10 eq) in the presence if DICI (10 eq) in anhydrous DMF. The Boc group was cleaved in the presence of trifluoroacetic acid (TFA) in dichloromethane (DCM) (55:45) for 30 min and the amine was neutralized by washing the resin with a 5% solution of DIEA in DCM. The free amine was treated with 4,6-dichloropyrimidine (10 eq) in dioxane at 100° C. for 24 hours. The second chloro group was displaced by treatment of the resin with piperazine (10 eq) in dioxane for 24 hours at 100° C. The free amine of the piperazine ring was acylated with a variety of commercially available carboxylic acids (10 eq) in the presence of DIC. The final desired compound was released from the resin by conventional HF cleavage at 0° C. for 1.5 hours, and then extracted, lyophilized and purified by preparative HPLC. The products were confirmed by LC-MS and NMR analysis.

Example 2: Characterization of Antifibrotic Compounds

Identification of Antifibrotic Compounds:

Compounds with antifibrotic activity were identified using a phenotypic assay based on the measurement of type 1 collagen synthesis and screening compounds in the Torrey Pines Institute (TPIMS) combinatorial libraries.

Measurement of collagen polypeptides in the cellular medium by western blot was used as the phenotypic assay of the profibrotic potential of cells. The four active compound structures in FIG. 2 were identified as structures that that may reduce type 1 collagen production. Positional libraries of one structure (TPI-2435) were deconvoluted. Deconvolusion of the TPI-2435 structures yielded at least twenty active antifibrotic compounds, which may reduce fibrosis of multiple organs, and can be developed into antifibrotic pharmaceutical dosage forms.

In order to maximize resources, the TPIMS Scaffold Ranking Library was developed. The Scaffold Ranking library of 30 million compounds provided a method to triage the available TPIMS 75 small molecule libraries based on activity in a given assay. Each mixture sample contained an equimolar concentration of every compound of a given scaffold. In this manner, the different core scaffolds available in the TPIMS collection could be compared based on activity. The present study sought to identify the best scaffold library for reducing the secretion of type I collagen from cultured cells.

Seventy five scaffold pools were prepared by TPIMS and were added to human lung fibroblasts in culture at a 90 μg/ml concentration. This concentration was used because testing was performed on the mixture-based libraries.

Figure 2:
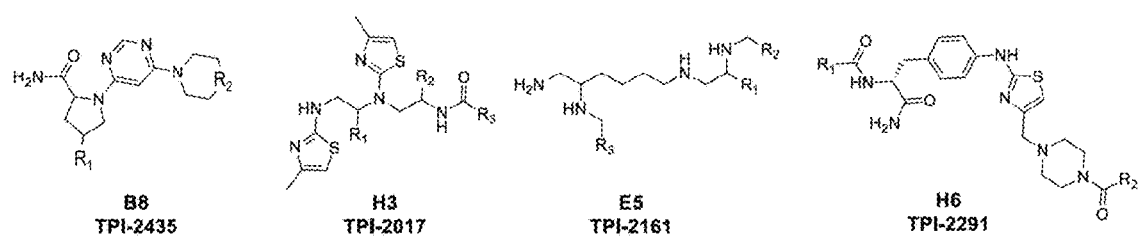
FIG. 2 is a set of chemical formulas for compounds selected for experimental antifibrotic testing.

Secretion of collagen $\alpha1(I)$ and $\alpha2(I)$ polypeptides into the cellular medium was measured by western blot after 72 hours. The prolonged incubation was done to select for the scaffold pools that were not toxic to the cells. Some pools showed substantial cell death after 72 hours and they were excluded from the analysis. For analysis of collagen secretion, the cellular medium was replaced after 72 hours with fresh medium and de novo collagen accumulation was allowed to proceed for 3 hours. An aliquot of the medium was then directly analyzed by western blot, while secretion of fibronectin was measured as control for specificity. Some pools (B8, E5 and H3), based on the scaffolds shown in FIG. 2, specifically reduced excretion of collagen $\alpha1(I)$ and $\alpha2(I)$ polypeptides, while the other pools were less active (H6) or inactive (D2, F5, G2). The pools B8 and H3 and E5 correspond to the scaffold libraries TPI-2435, TPI-2017 and TPI-2165 respectively (FIG. 2).

Figure 3:
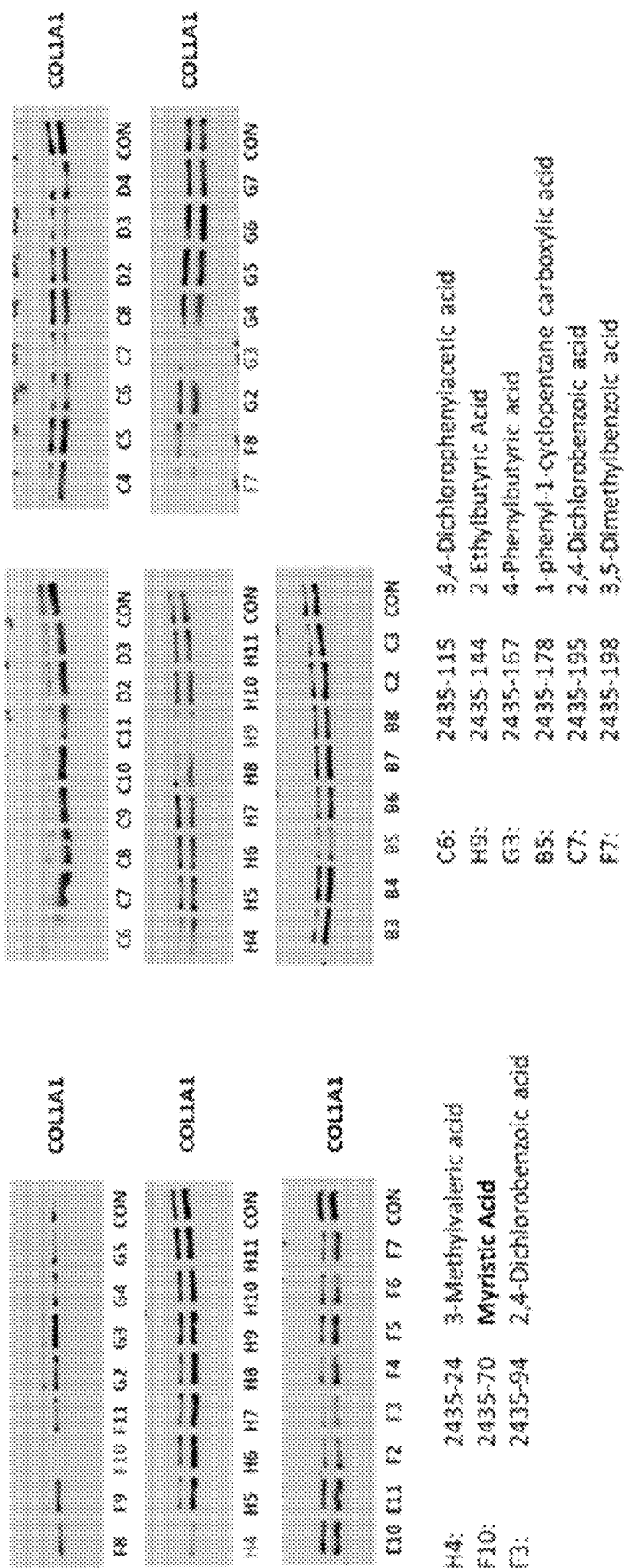
FIG. 3 is position scanning screen data for the specified compounds.

Positional Scanning Screening of the TP-2435 Library:

The library TP-2435 was selected for positional scanning screening experiments. The compounds were added at 10 μg/ml to human lung fibroblasts and collagen $\alpha1(I)$ polypeptide was measured in the cellular medium. Results from a portion of this screen are shown in FIG. 3. Several mixtures were active in inhibiting type 1 collagen at 10 μg/ml. Three mixtures (F10, H4 and F3) in which the first position R1 and six mixtures in which the R2 position is defined showed good inhibition activity. The synthesis and screening of all the individual compounds making all the combinations of active R1 and R2 is described below as deconvolusion of the library TPI-2435.

Individual Compounds Made for Control of Synthesis Show Collagen Inhibition:

In addition to the mixtures, 202 individual compounds were also evaluated as synthesis and/or diversity controls for each scaffold library. These controls are shown in FIGS. 5A-5K and FIGS. 6A-6B. They were prepared in parallel to the synthesis of the mixture based library TPI-2435 as controls to determine whether the individual building blocks used at each of the variable positions could be successfully incorporated into the synthesis of the mixture libraries. The 202 different individual compounds (All the 101 different carboxylic acids for R1 position while the R2 position is fixed with phenyl acetic acid, and all the 101 different carboxylic acids for R2 position while the R1 position is fixed with phenyl acetic acid) were tested.

Figure 4:
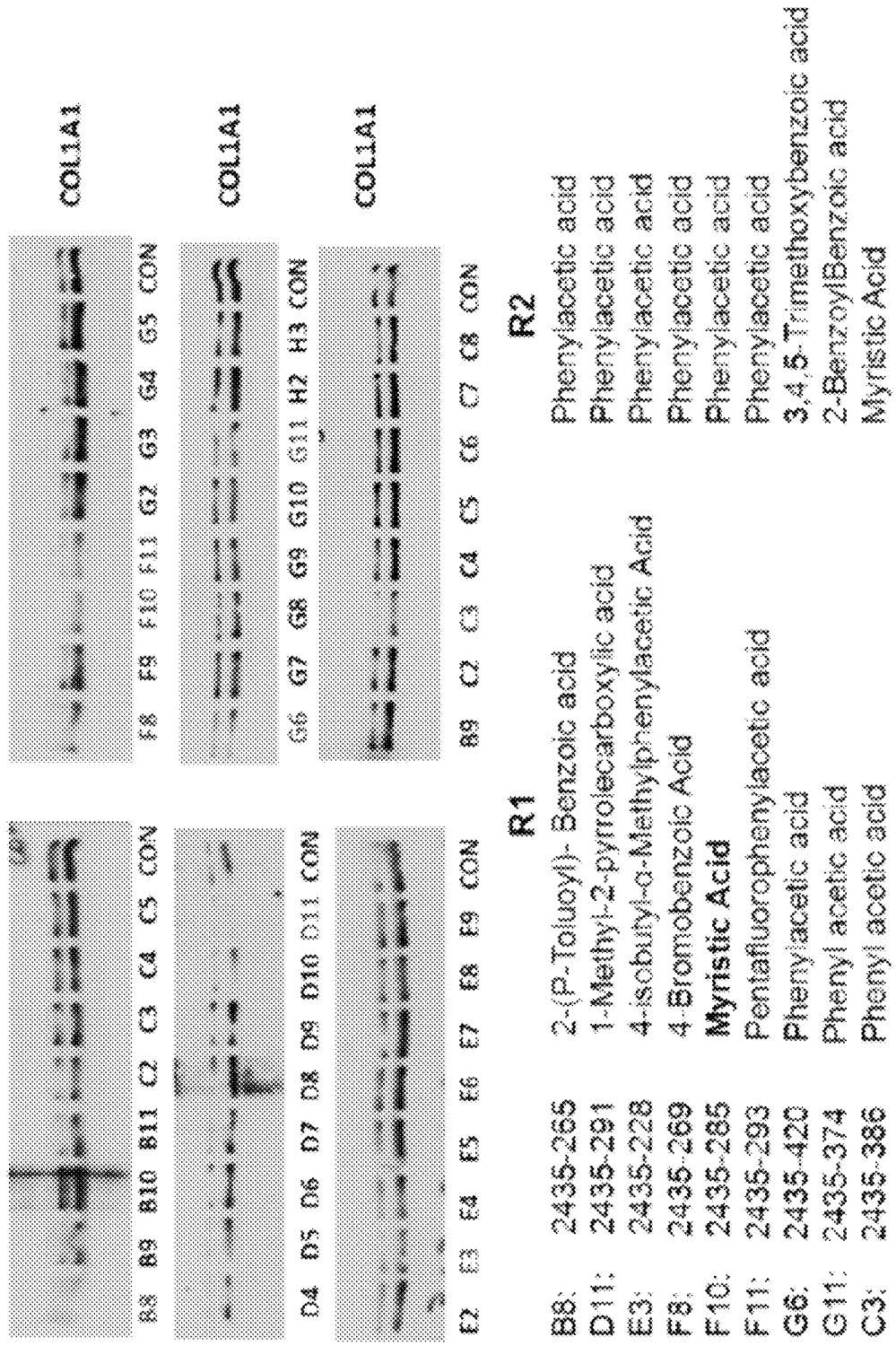
FIG. 4 is position scanning screen data for the individual control compounds specified.
Figure 5A:
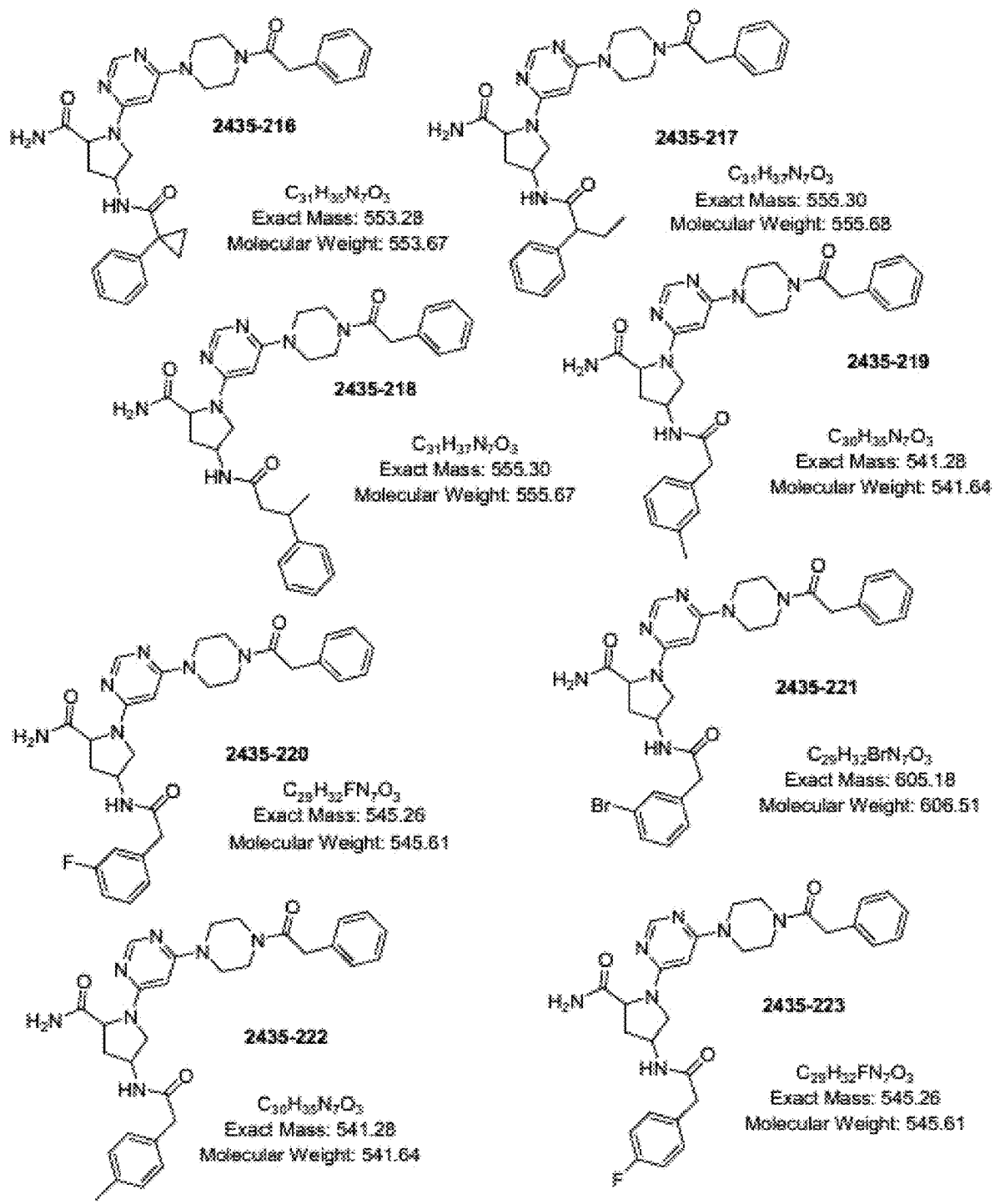
FIG. 5A is a set of chemical structures of the individual controls prepared in parallel with the TPI-2435 compounds.
Figure 5B:
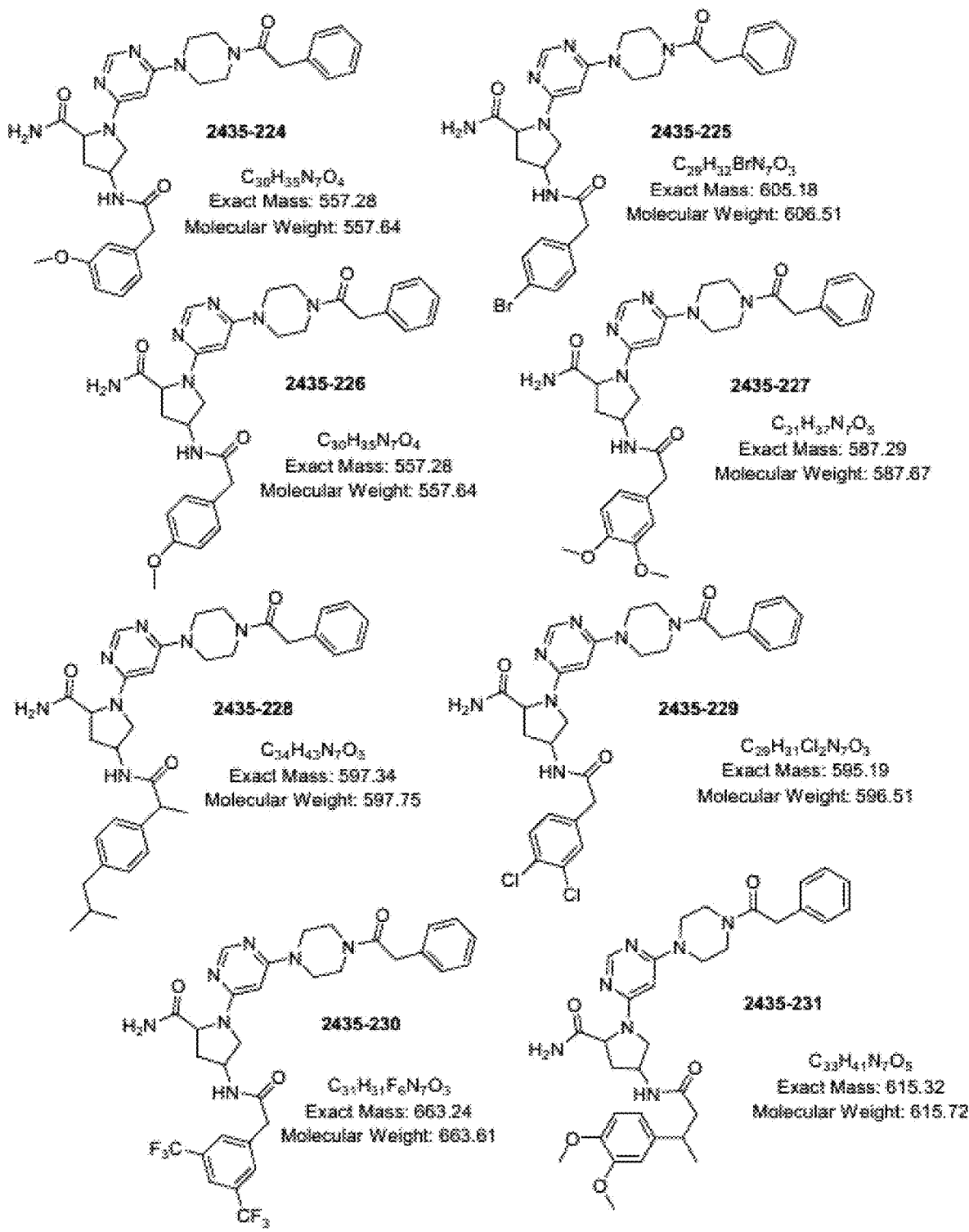
FIG. 5B is a continuation of FIG. 5A.
Figure 5C:
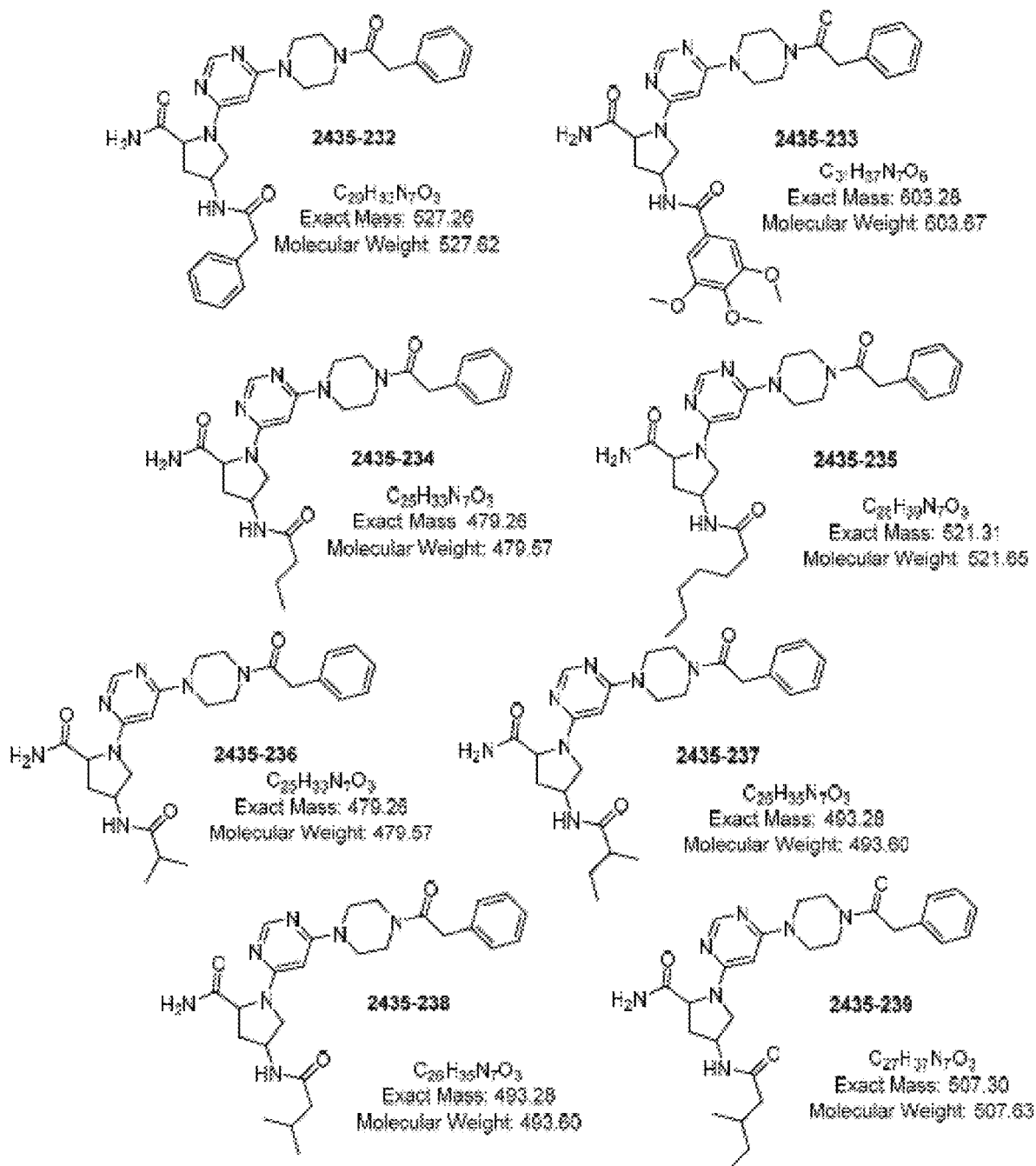
FIG. 5C is a continuation of FIG. 5A.
Figure 5D:
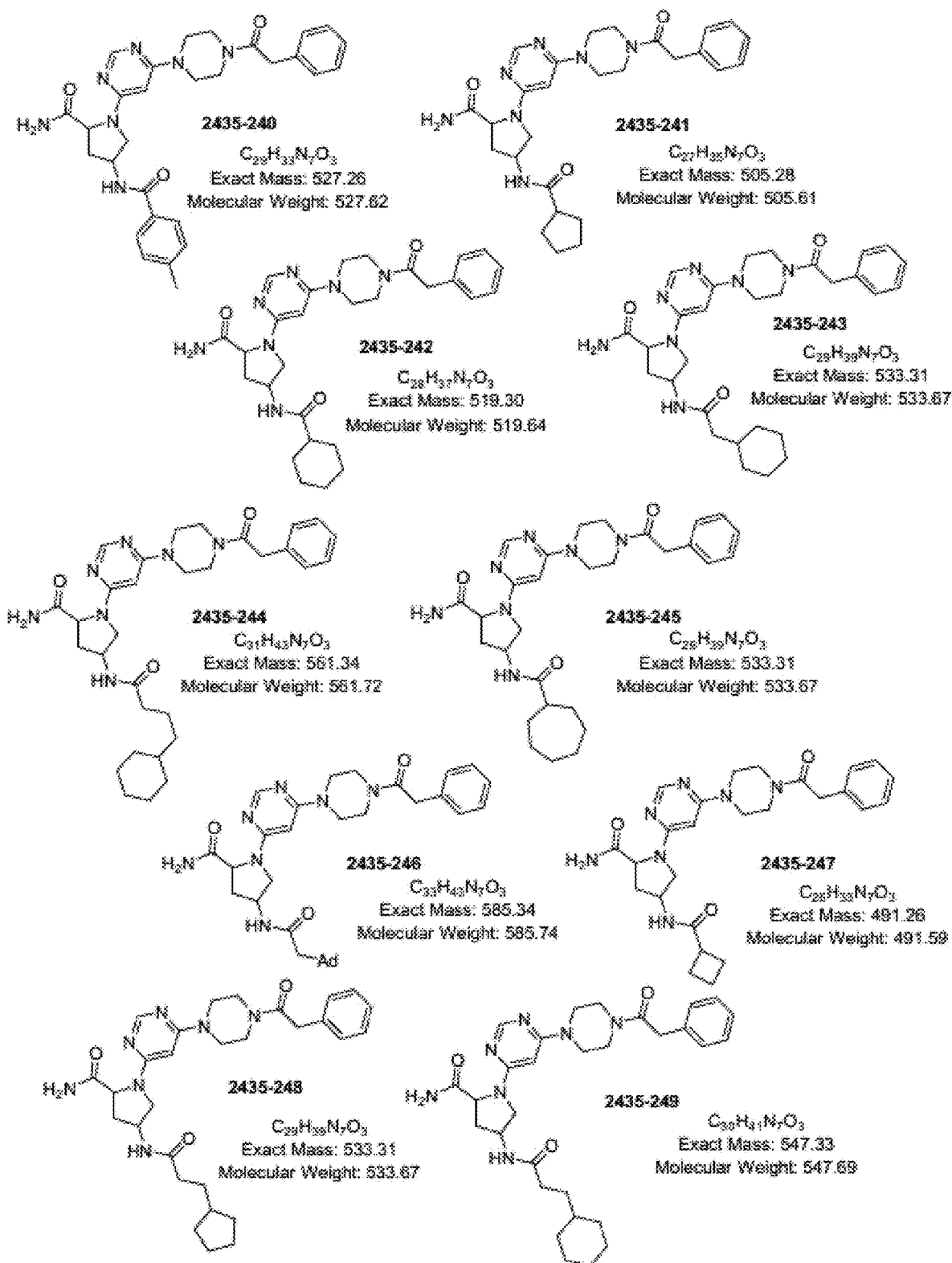
FIG. 5D is a continuation of FIG. 5A.
Figure 5E:
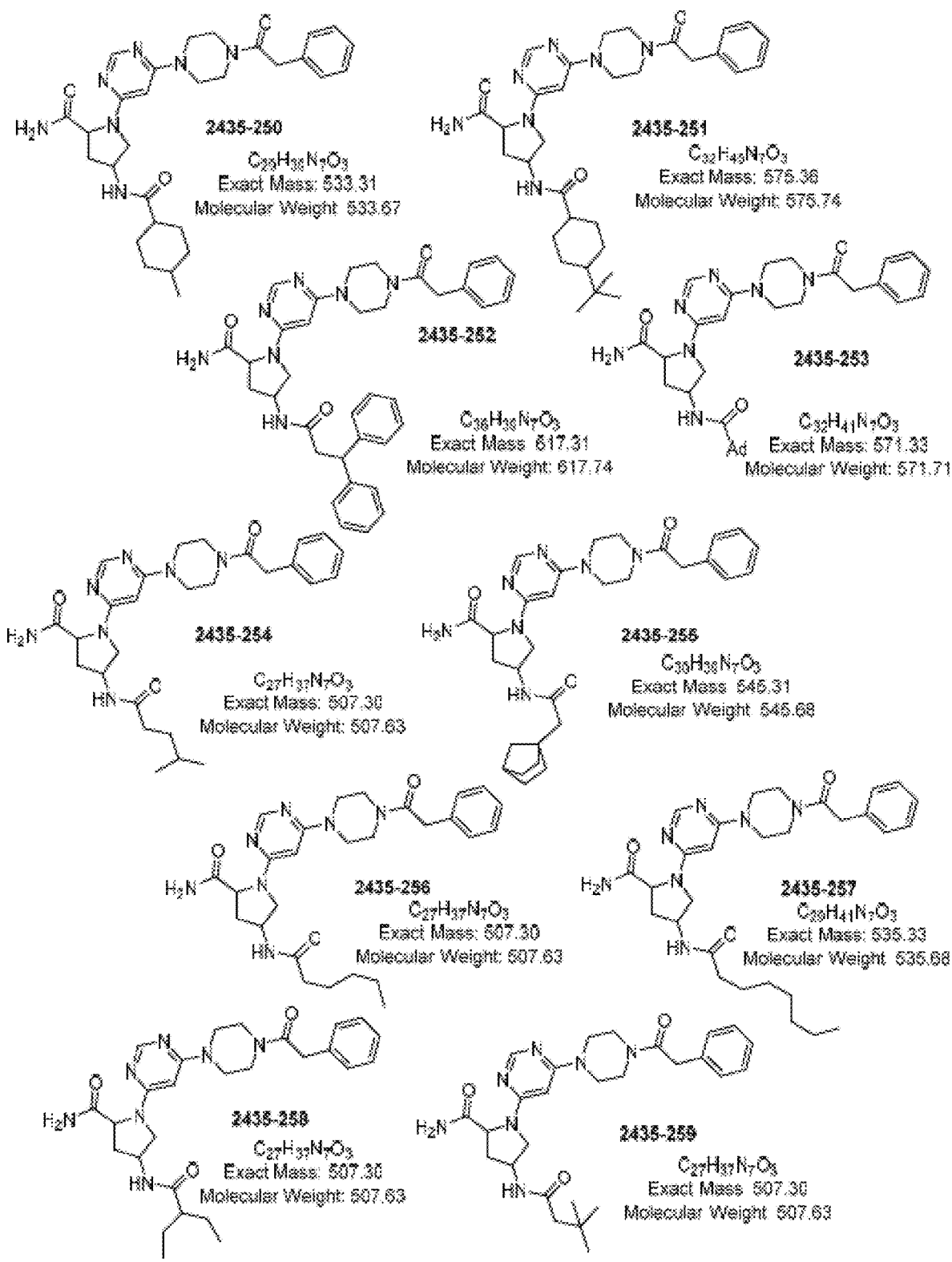
FIG. 5E is a continuation of FIG. 5A.
Figure 5F:
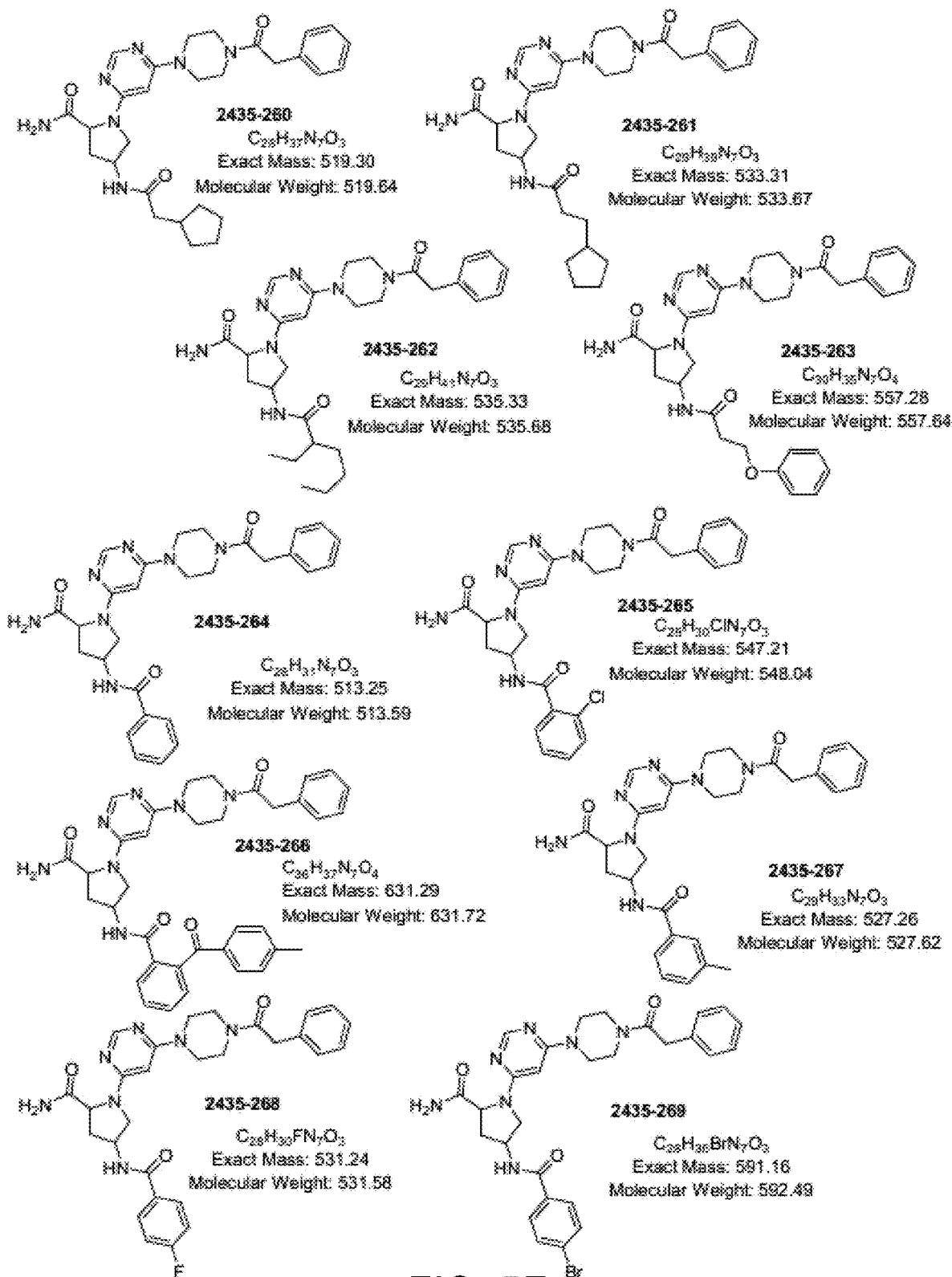
FIG. 5F is a continuation of FIG. 5A.
Figure 5G:
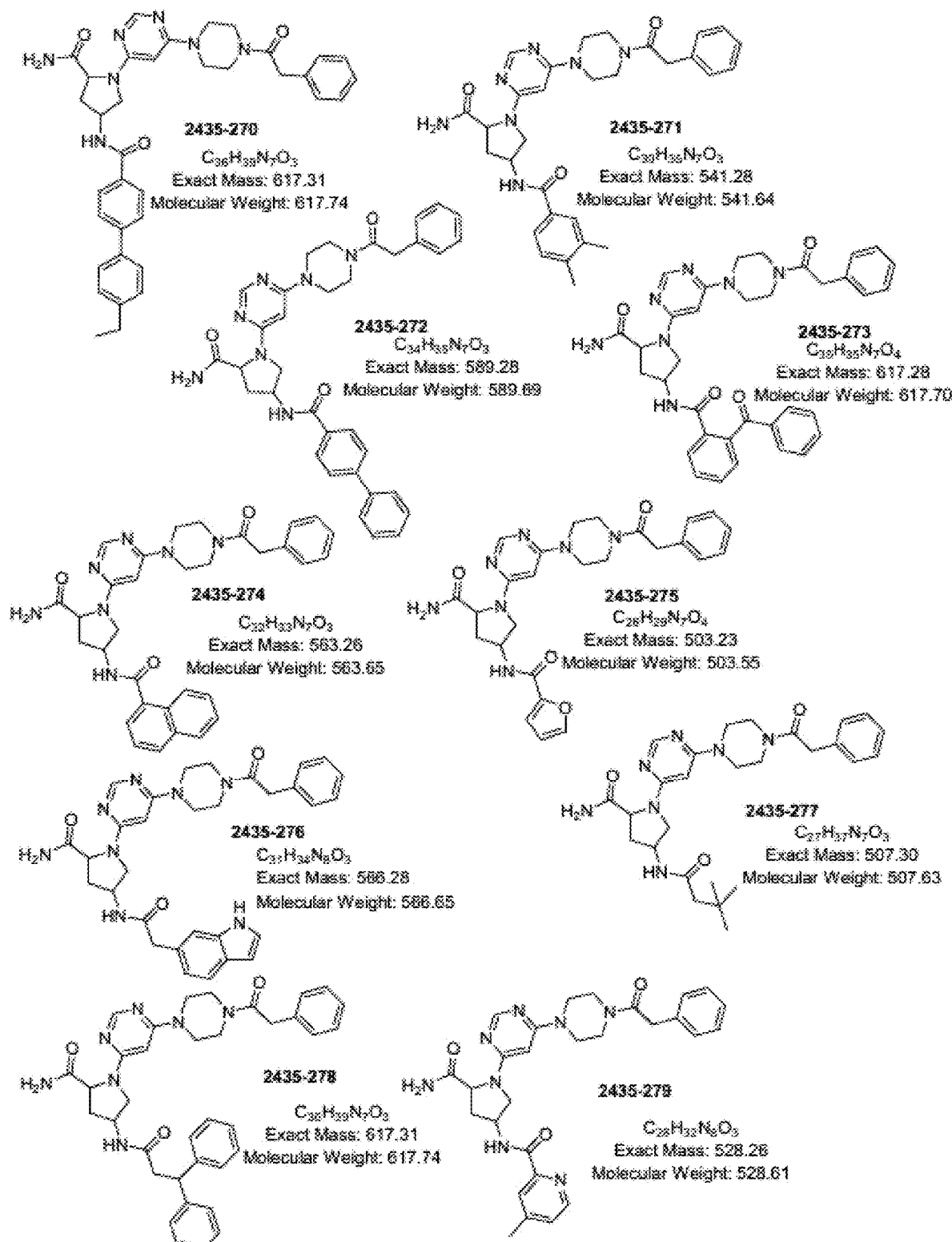
FIG. 5G is a continuation of FIG. 5A.
Figure 5H:
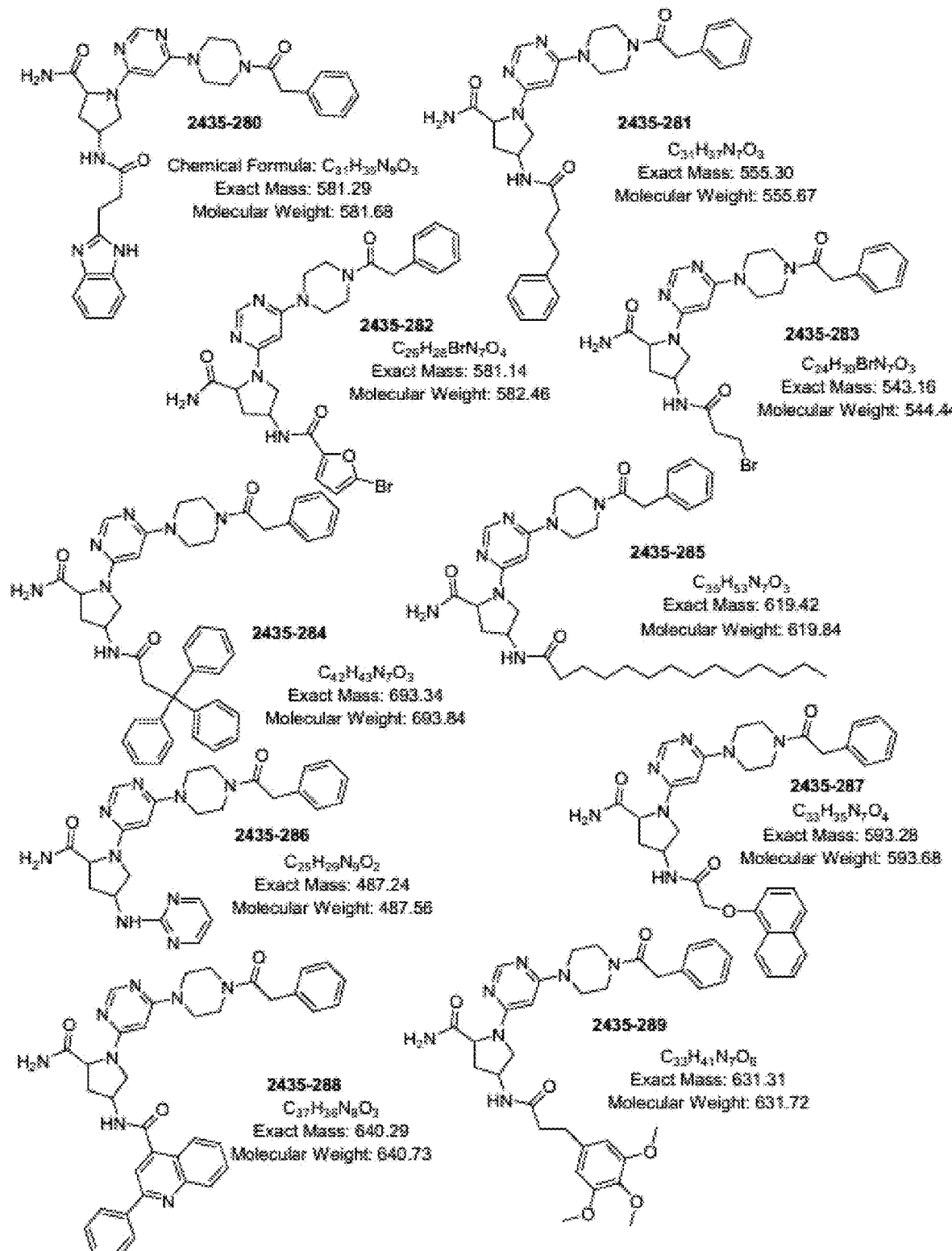
FIG. 5H is a continuation of FIG. 5A.
Figure 5I:
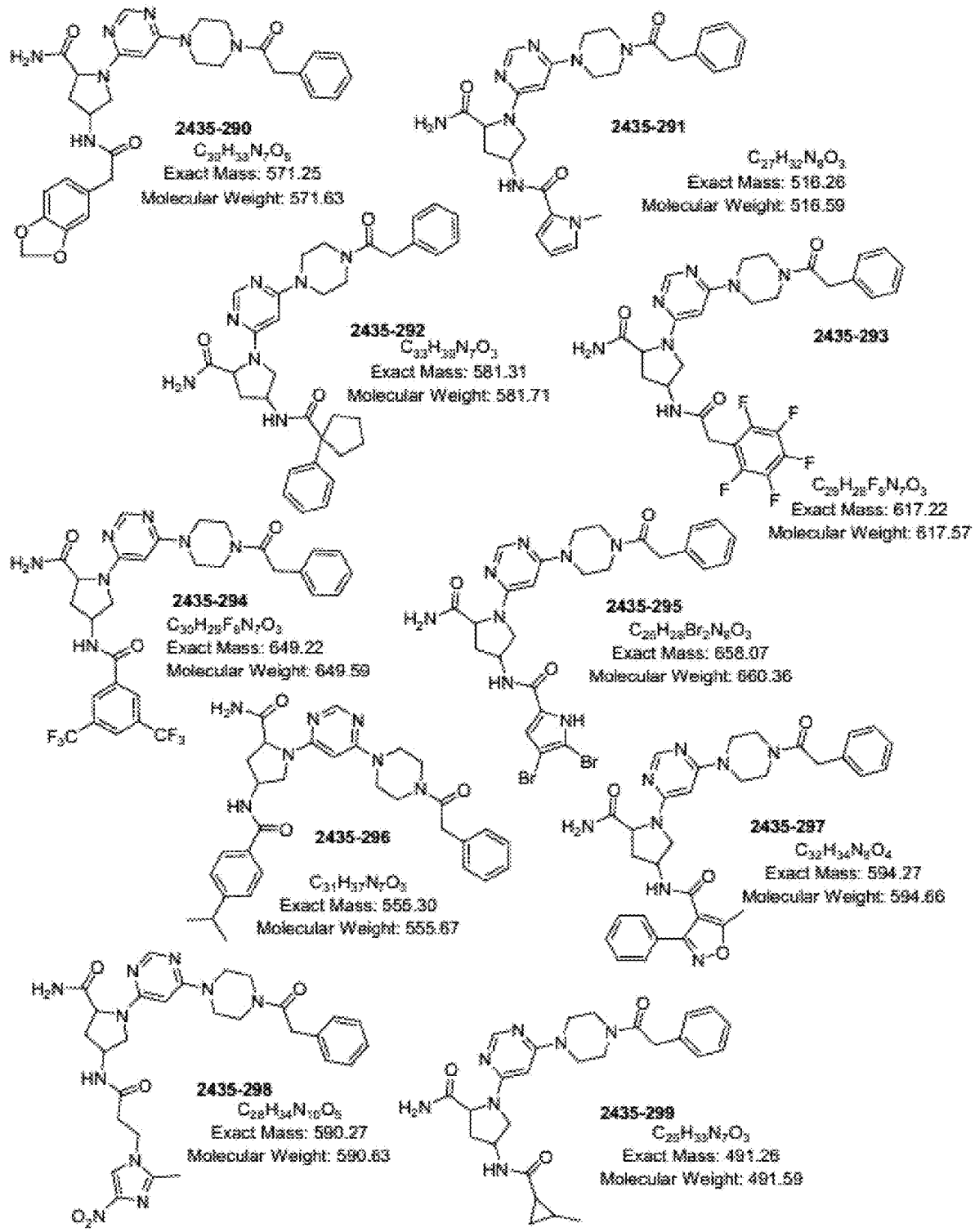
FIG. 5I is a continuation of FIG. 5A.
Figure 5J:
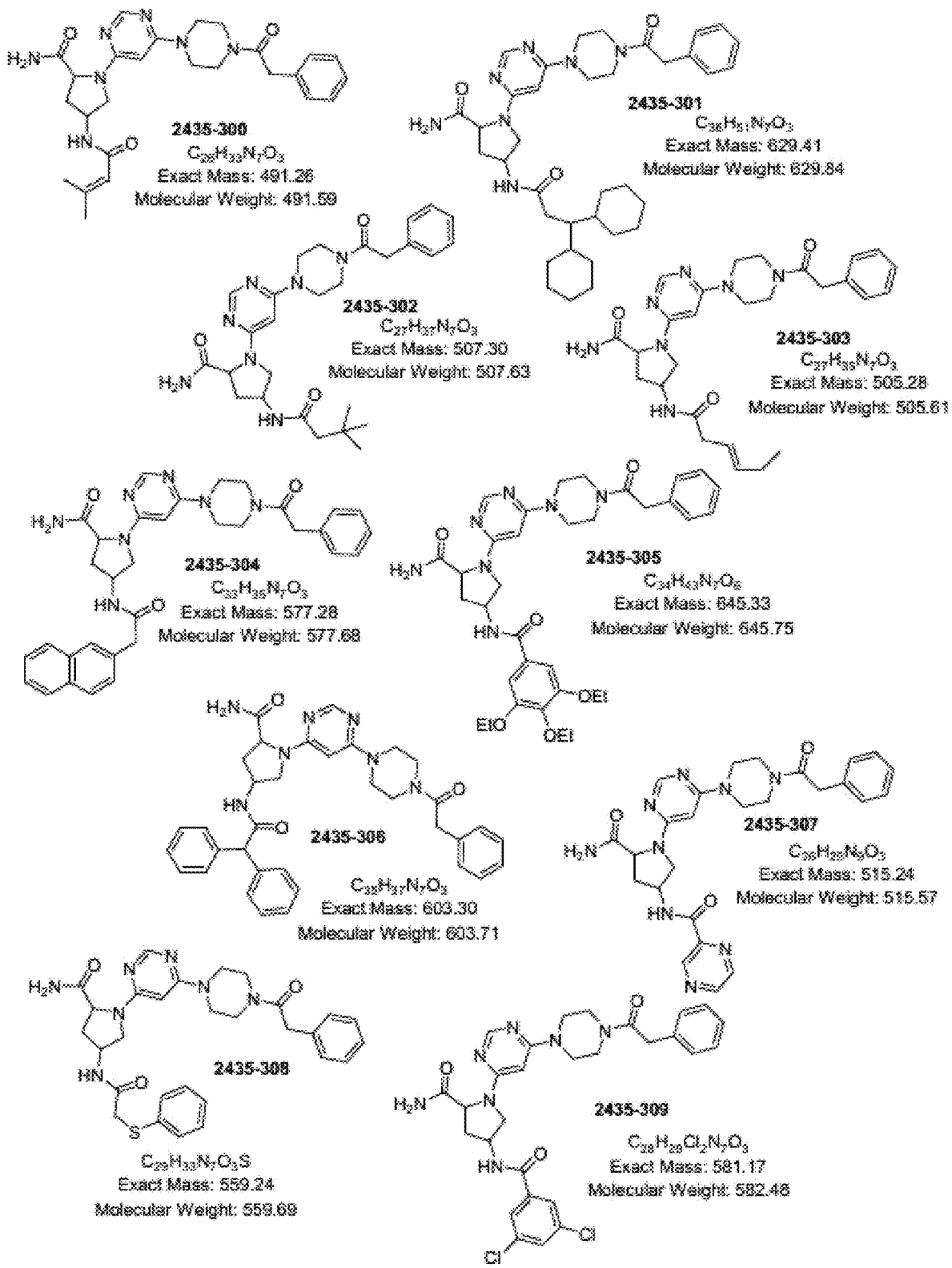
FIG. 5J is a continuation of FIG. 5A.
Figure 5K:
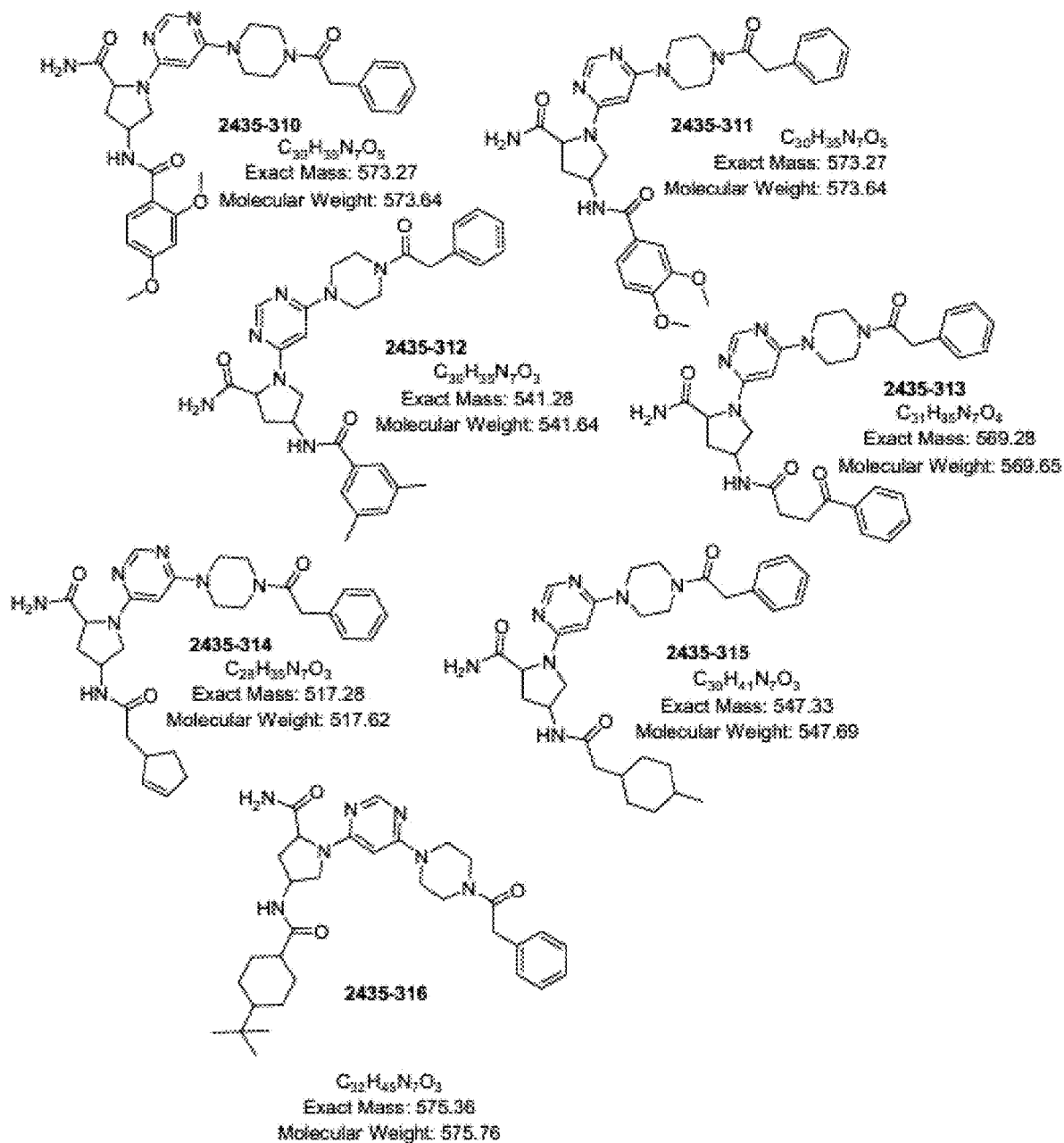
FIG. 5K is a continuation of FIG. 5A.
Figure 6A:
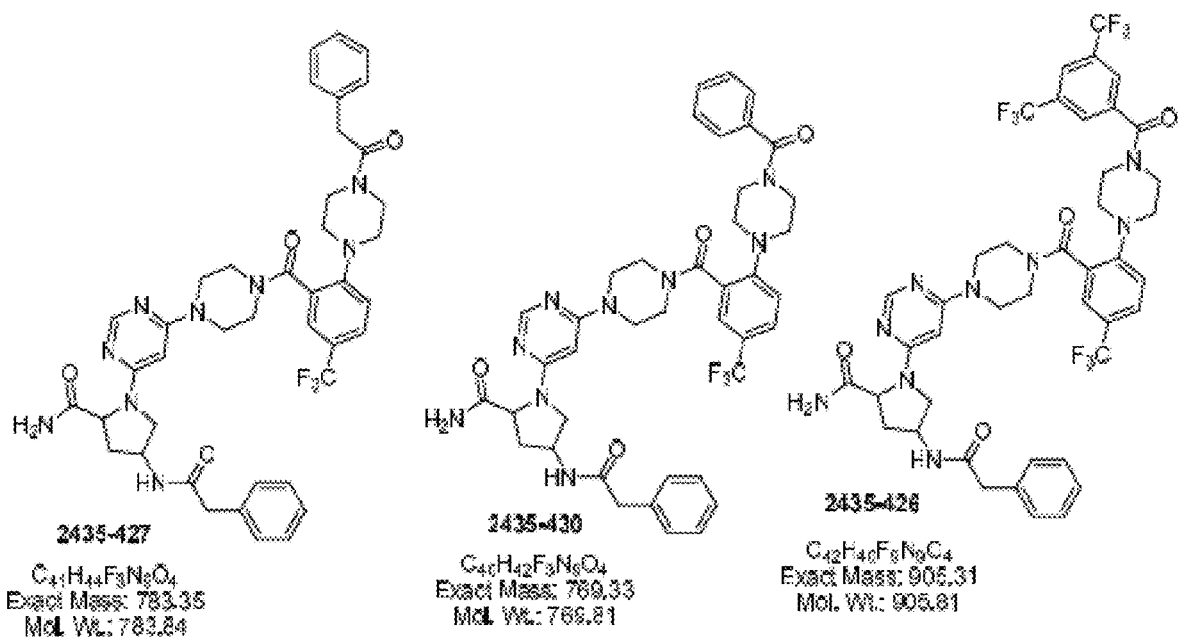
FIG. 6A is a set of chemical structures of other individual controls.
Figure 6A:
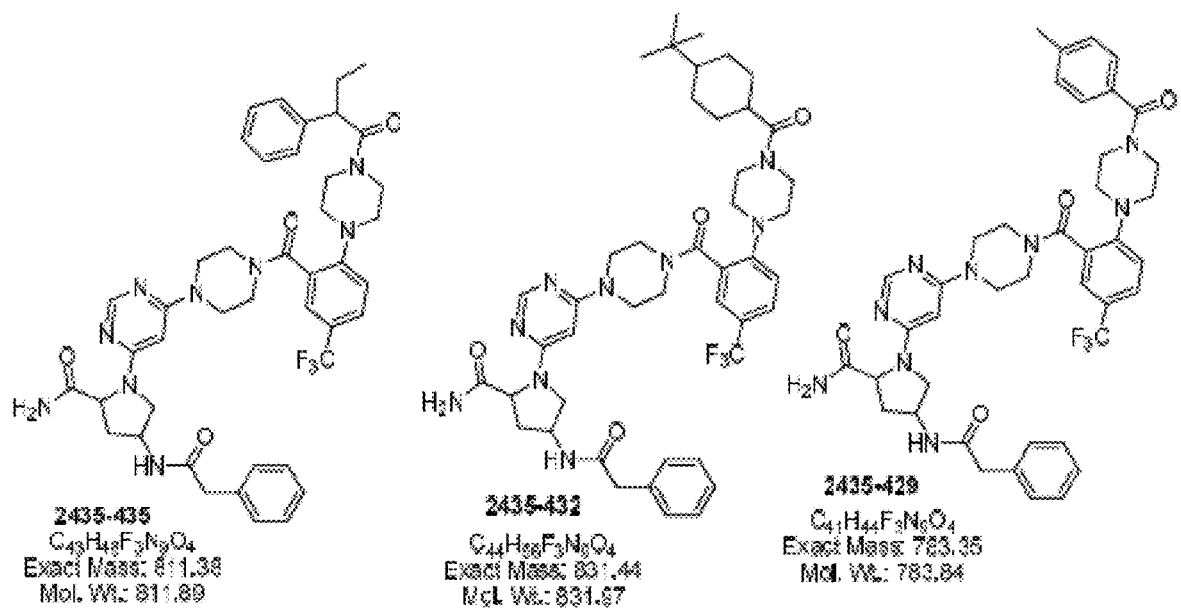
Figure 6B:
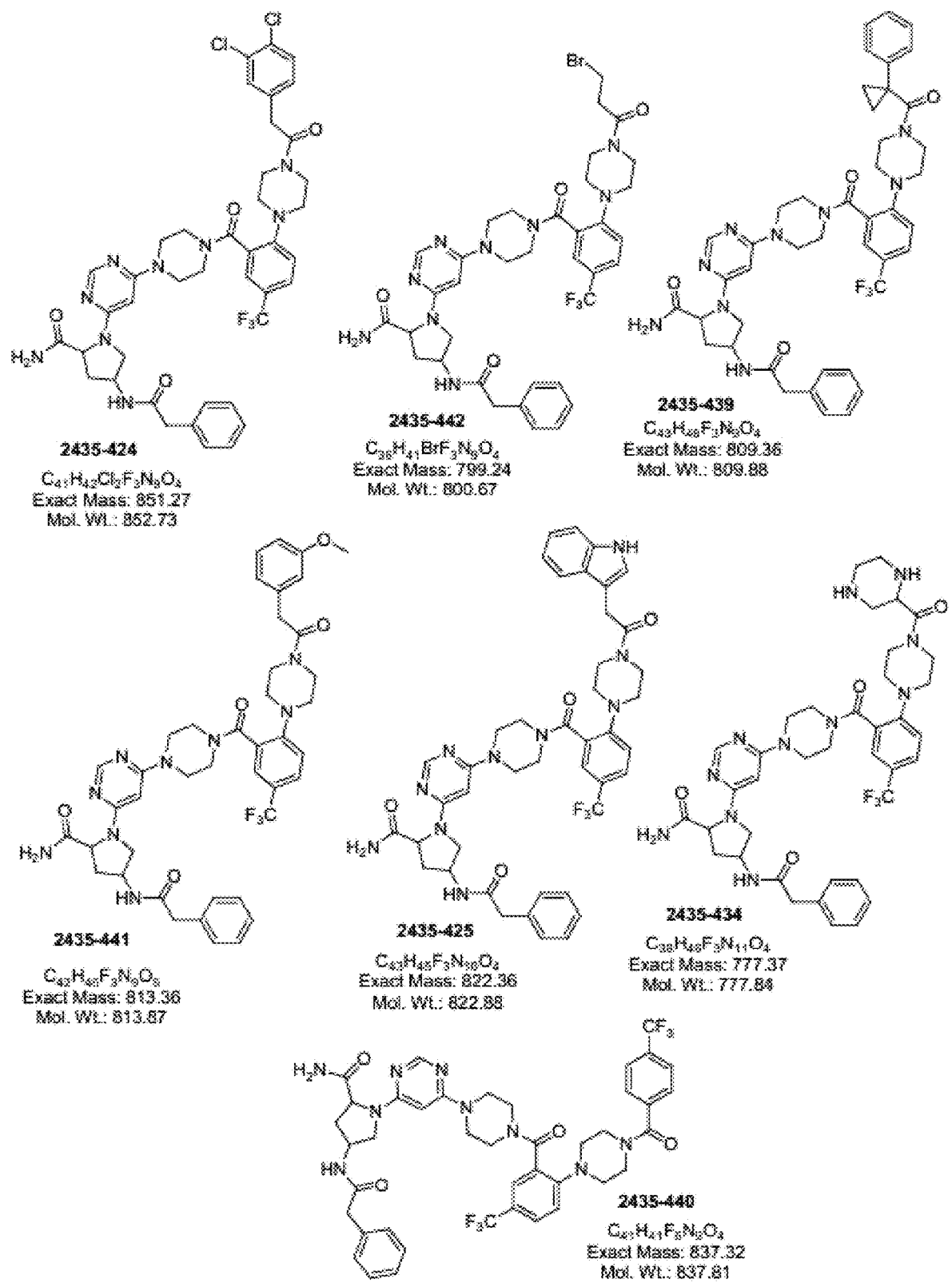
FIG. 6B is a continuation of FIG. 6A.
Figure 7A:
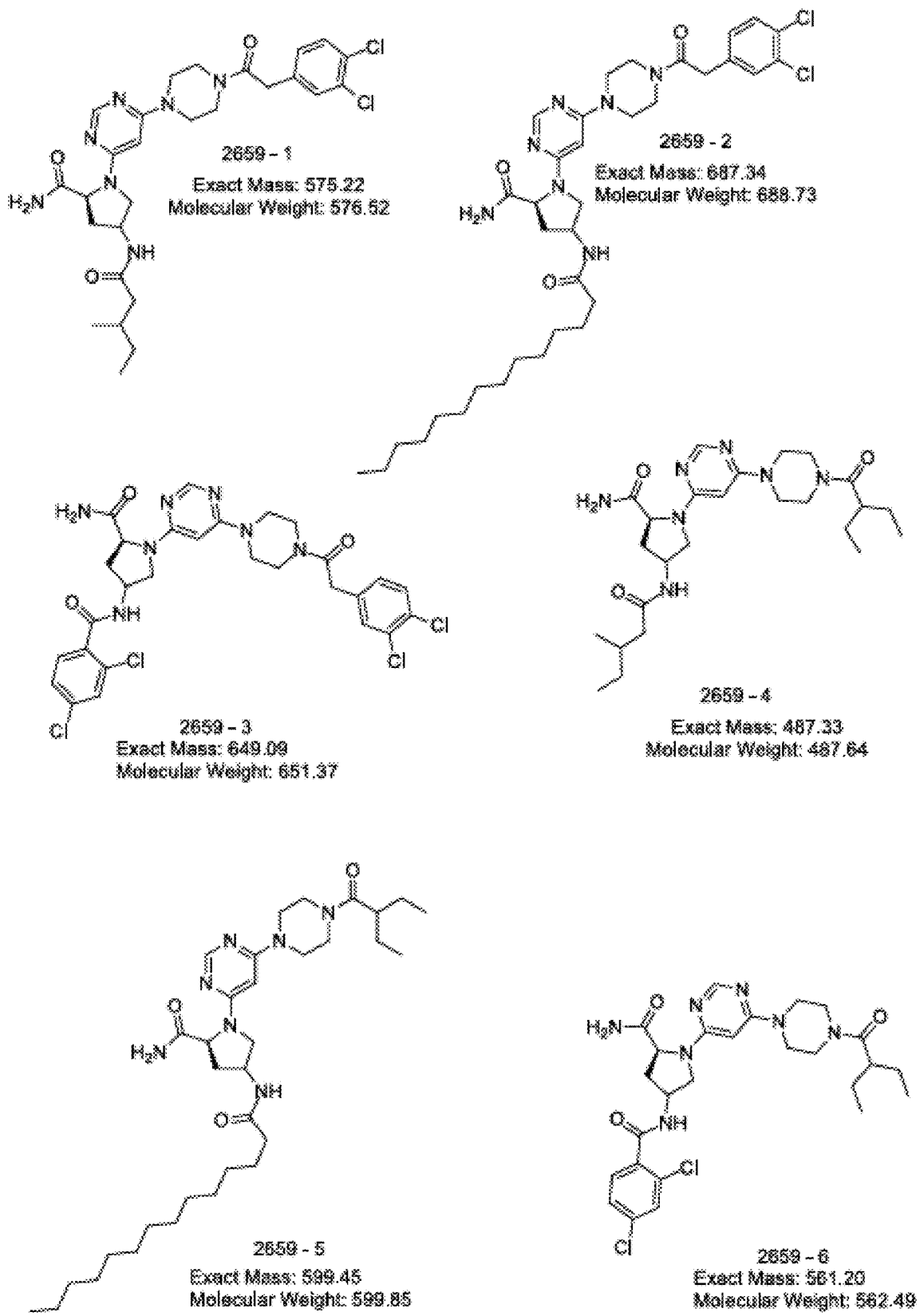
FIG. 7A is set of chemical structures of the compounds with the active R1 and R2 groups of the TPI-2435 compounds, which is referred to herein as the TPI-2659 compounds.
Figure 7B:
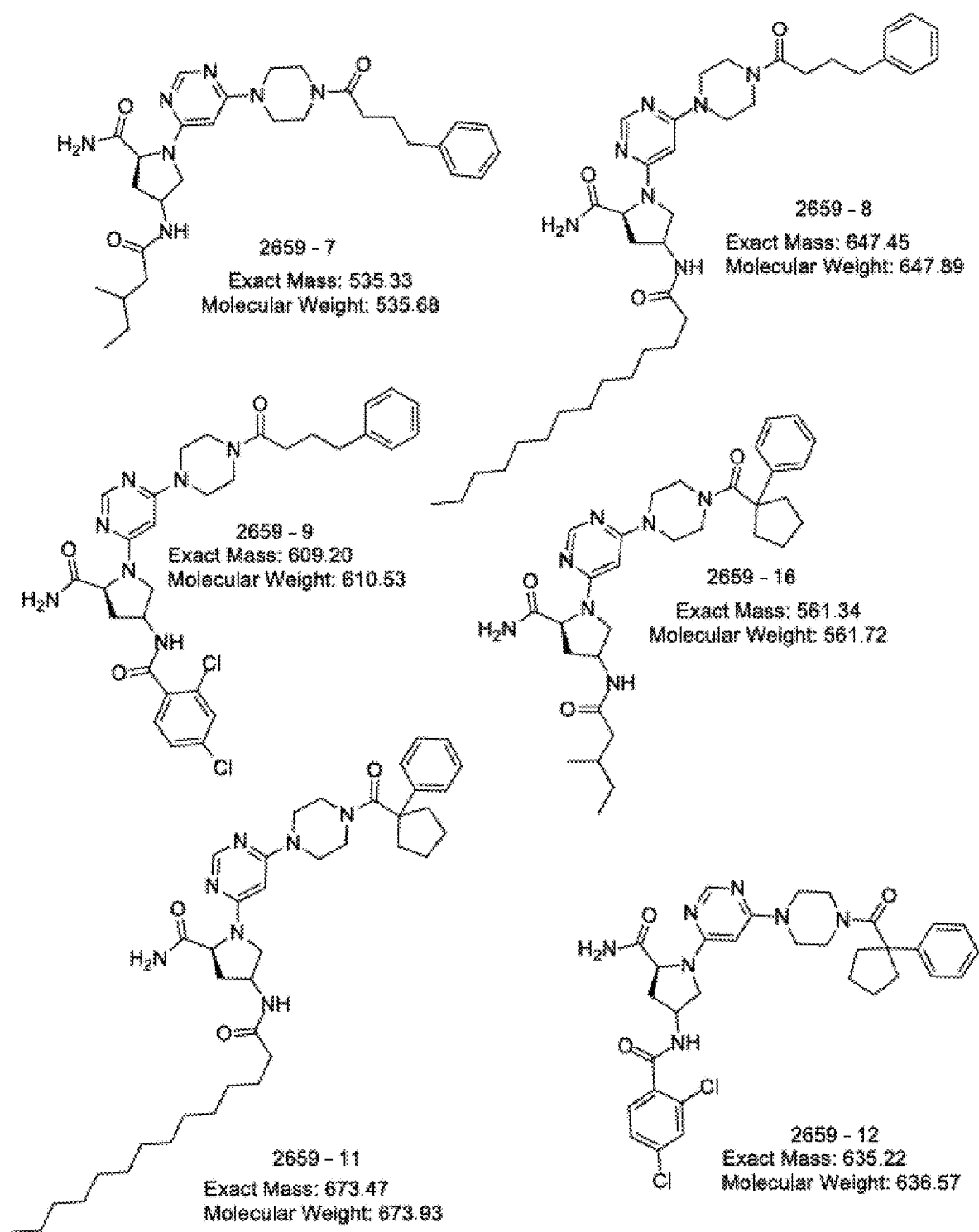
FIG. 7B is a continuation of FIG. 7A.
Figure 7C:
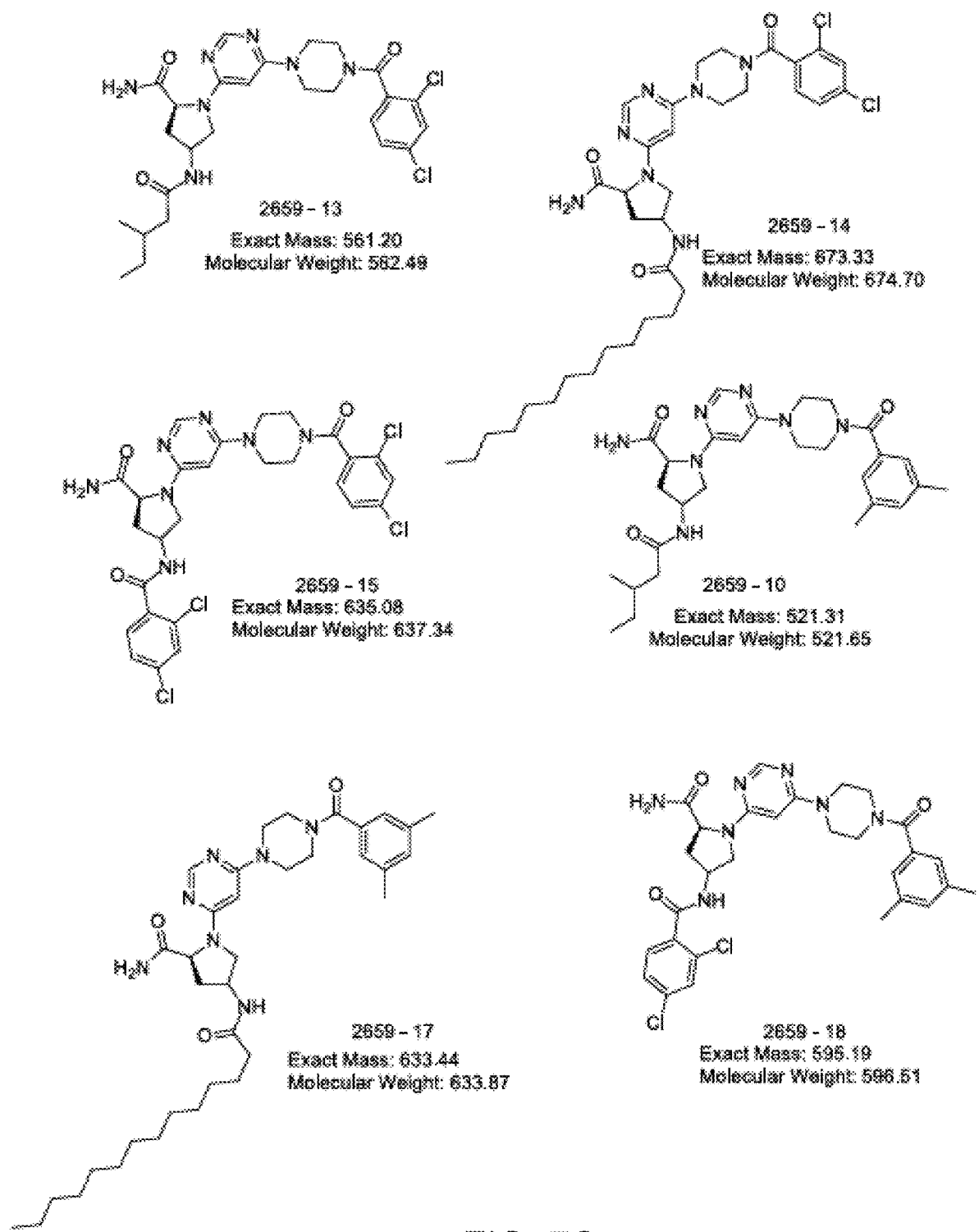
FIG. 7C is a continuation of FIG. 7A.
Figure 7D:
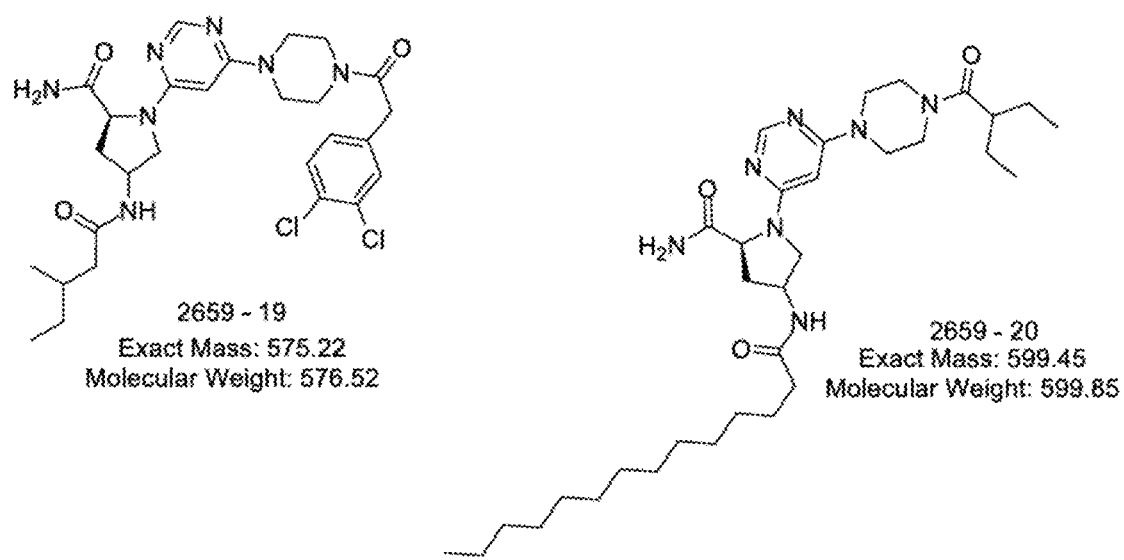
FIG. 7D is a continuation of FIG. 7A.

The screening of the 202 control compounds led to the identification of active inhibitors of type I collagen. As shown in FIG. 4, nine compounds were identified as inhibitors of COLA1 at 10 μg/ml. The compounds with R1=myristic acid is active as was observed for the mixture. This was a strong indication that the complete deconvolution of the library would lead compounds with significantly improved potency.

Individual active controls from the library TPI-2435 (compounds: 265, 291, 228, 269, 285) elicited strong activity despite having a phenyl acetic acid group at position R2, which is not among the most active mixtures. These results encouraged the full deconvolution of the libraries to identify more potent hits by incorporating the optimal modifications in all R group positions Deconvolution of the Positional Scanning Library TPI-2435:

In the positional scanning screening of the library TPI-2345, three mixtures (F10, H4 and F3) in which the first position R1 is defined and six mixtures (C6, H9, G3, B5, C7, F7) in which the position R2 is defined showed good inhibition activity. Parallel synthesis and screening of all the individual compounds was performed, making all the combinations of active R1 and R2. The new eighteen compounds are referred to herein is TPI-2659 library. The structure of these compounds is shown in FIGS. 7A-7D.

Figure 8:
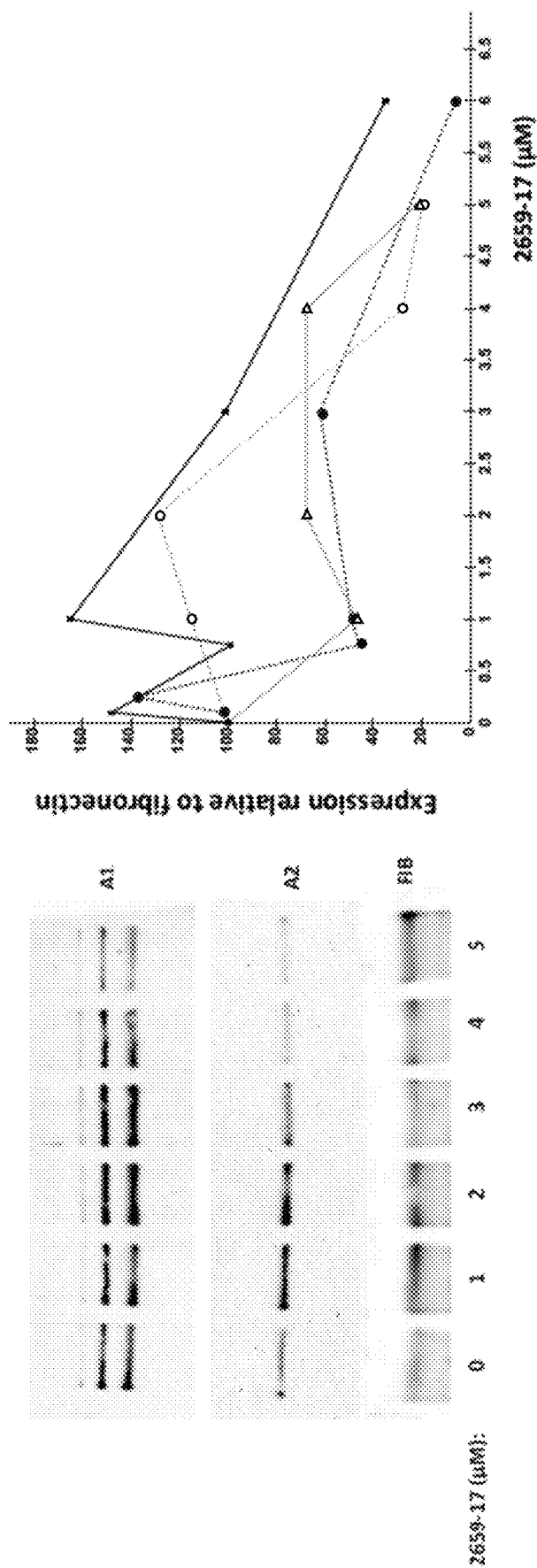
FIG. 8 is experimental data showing the efficacy of compound 2659-17 on inhibition of type 1 collagen secretion by human lung fibroblasts. The left panel is a western blot of procollagen α(1) polypeptide (A1), procollagen α(2) polypeptide (A2), and fibronectin (FIB) secreted from cells treated with the specified concentration of 2659-17. The right panel is a graph of the inhibition in two independent experiments. The solid symbols are data for of procollagen α(1) polypeptide. The open symbols are for of procollagen α(2) polypeptide.

Efficacy and Mechanism of Action of Compound 2659-17:

Compound 2659-17 was further tested for inhibition of the collagen $\alpha1(I)$ and $\alpha2(I)$ polypeptides in a range of concentrations (FIG. 8). The left panel in FIG. 8 shows a representative western blot where it is clearly seen that the secretion of the collagen $\alpha1(I)$ polypeptide was inhibited at 5 μM and that of collagen $\alpha2(I)$ polypeptide at 4 μM. The secretion of fibronectin was not affected with this compound, suggesting that it does not inhibit the general protein secretion pathway, but that it has specific activity towards type 1 collagen. The right panel shows the dose dependent inhibition of the α1(I) and α2(I) polypeptides obtained in two independent experiments. The curves indicate a clear inhibitory potential at doses >4 μM.

Because LARP6 is one of the regulators of type I collagen production in fibrosis, experiments were performed to assess if 2659-17 inhibits type 1 collagen production by interfering with the LARP6 function. LARP6 functions by binding the unique 5' stem-loop structure present in type I collagen mRNAs (5'SL), thus compound 2659-17 was tested to determine whether it can inhibit the LARP6/5'SL binding.

Two domains of LARP6, the La-domain (La) and the RRM, together called the La-module (LaM), contribute to the high affinity of binding to the 5'SL RNA motif. The La-domain alone binds 5'SL in sequence specific manner, while the presence of RRM increases the affinity of binding. To assess if 2659-17 can inhibit the binding of La-domain, as well as that of higher affinity binding of La-module we prepared these recombinant proteins, mixed them with fluorescently labeled 5'SL RNA (5'SL) and added 2659-17 to these in vitro binding reactions.

Figure 9:
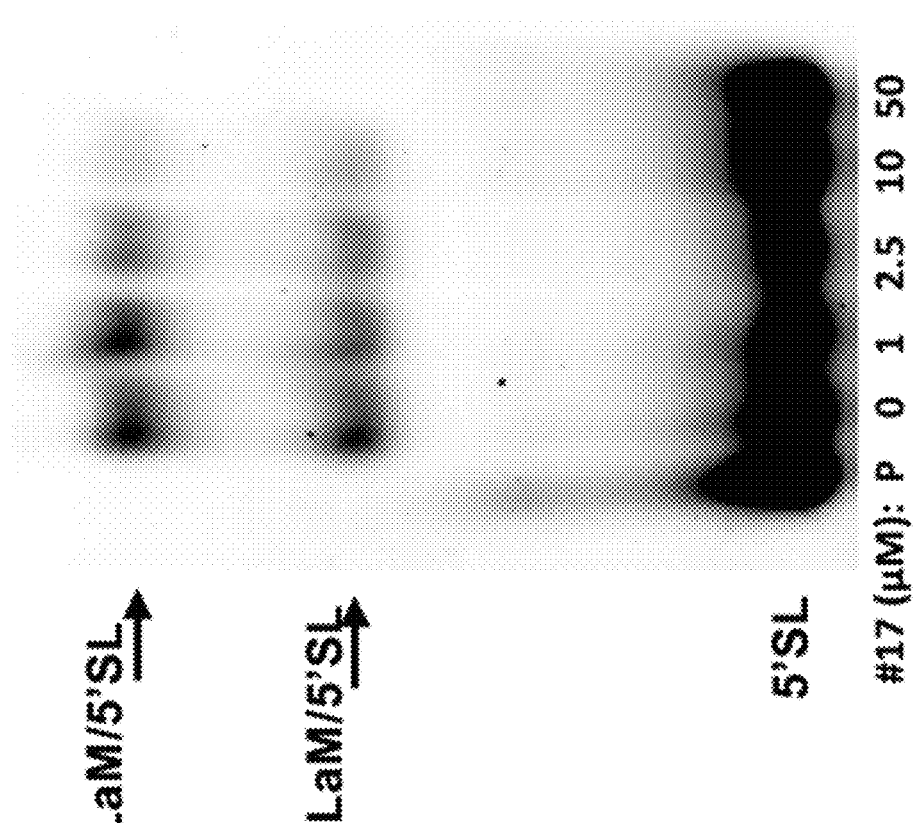
FIG. 9 is experimental data of the inhibition of LARP6 binding to the 5' stem loop of collagen mRNAs. The left panel gel is a mobility shift assay with the recombinant La-domain (left panel) and La-module (right panel) and fluorescently-labeled 5' stem loop RNA. The migration of the free RNA and protein/RNA complexes and the concentration of compound 2659-17 is specified.
Figure 9:
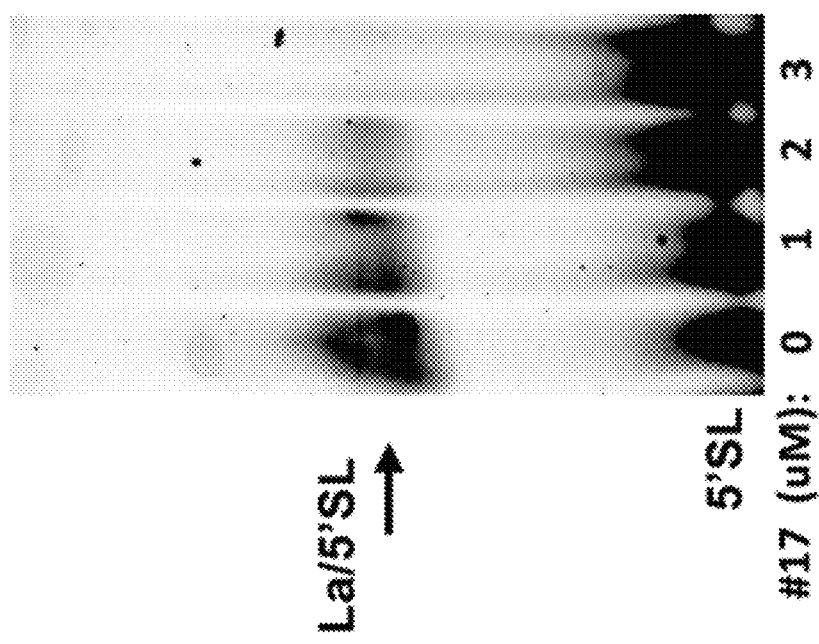

The formation of protein/RNA complexes was monitored by a gel mobility shift assay experiment (FIG. 9). In the absence of compound 2659-17 an RNA/protein complex was formed between the La-domain and 5'SL (La/5'SL). The intensity of this complex started to diminish with 1 μM of 2659-17 and the complex disappeared at 3 μM (FIG. 9, left panel). With the La-module, two protein/RNA complexes were seen (LaM/5'SL), which represent the formation of monomer and dimer of the La-module with 5'SL RNA. Compound 2659-17 inhibited the formation of both complexes starting at concentration of 2.5 μM, while the complexes were eliminated at 40 μM (right panel). The higher concentration needed for the inhibition of La-module binding reflects the higher affinity of this module for 5'SL RNA.

Table 1 is a list of the compounds of Formula 1 tested. R1 and R2 are specified. R3=H2N—C═O. The "X" in certain entries represents that the R3 or R2 represented by the X was a mixture of the specified R group examples.

TABLE 1

Examples of compounds of Formula 1 tested

| # | R1 | R2 |
|---|---|---|
| 1 | 1-phenyl-1-cyclopropanecarboxylic acid | X |
| 2 | 2-Phenylbutyric Acid | X |
| 3 | 3-Phenylbutyric Acid | X |
| 4 | m-Tolylacetic acid | X |
| 5 | 3-Fluorophenylacetic Acid | X |
| 6 | 3-Bromophenylacetic Acid | X |
| 7 | p-Tolyacetic acid | X |
| 8 | 4-Fluorophenylacetic acid | X |
| 9 | 3-Methoxyphenylacetic acid | X |
| 10 | 4-Bromophenylacetic acid | X |
| 11 | 4-Methoxyphenylacetic acid | X |
| 12 | 3,4-Dimethoxyphenylacetic acid | X |
| 13 | 4-isobutyl-alpha-Methylphenylacetic Acid | X |
| 14 | 3,4-Dichlorophenylacetic acid | X |
| 15 | 3,5-Bis(Trifluoromethyl)-Phenylacetic acid | X |
| 16 | 3-(3,4-Dimethoxyphenyl)-propionic Acid | X |
| 17 | Phenylacetic acid | X |
| 18 | 3,4,5-Trimethoxybenzoic acid | X |
| 19 | Butyric Acid | X |
| 20 | Heptanoic Acid | X |
| 21 | Isobutyric Acid | X |
| 22 | 2-Methylbutiric Acid | X |
| 23 | Isovaleric acid | X |
| 24 | 3-Methylvaleric acid | X |
| 25 | p-Toluic Acid | X |
| 26 | cyclopentanecarboxylic acid. | X |
| 27 | cyclohexanecarboxilic acid | X |
| 28 | cyclohexylacetic acid | X |
| 29 | cyclohexanebutyric acid | X |
| 30 | cycloheptanecarboxylic acid | X |
| 31 | 1-Adamantaneacetic Acid | X |
| 32 | cyclobutanecarboxylic acid | X |
| 33 | 3-cyclopentylpropionic acid | X |
| 34 | cyclohexanepropionic acid | X |
| 35 | 4-methyl-1-cyclohexancarboxylic acid | X |
| 36 | 4-tert-butyl-cyclohexancecarboxylic acid | X |
| 37 | 4-biphenylacetic acid | X |
| 38 | 1-Adamantancecarboxylic acid | X |
| 39 | 4-Methylvaleric acid | X |
| 40 | 2-norbornaneacetic acid | X |
| 41 | Hexanoic Acid | X |
| 42 | Octanoic Acid | X |
| 43 | 2-Ethylbutyric Acid | X |
| 44 | Trimethylacetic Acid | X |
| 45 | Cyclopentylacetic Acid | X |
| 46 | 3-Cyclopentylpropionic Acid | X |
| 47 | 2-ethylhexanoic | X |
| 48 | 2-Phenoxypropionic acid | X |
| 49 | Benzoic acid | X |

TABLE 1-continued

Examples of compounds of Formula 1 tested

| # | R1 | R2 |
|---|---|---|
| 50 | 2-Chlorobenzoic acid | X |
| 51 | 2-(P-Toluoyl)-Benzoic acid | X |
| 52 | m-Toluic acid | X |
| 53 | 4-Fluorobenzoic Acid | X |
| 54 | 4-Bromobenzoic Acid | X |
| 55 | 4-Ethylbiphenyl-4'-carboxylic acid | X |
| 56 | 3,4-Dimethylbenzoic acid | X |
| 57 | 4-Biphenylcarboxylic Acid | X |
| 58 | 2-BenzoylBenzoic acid | X |
| 59 | 1-Naphthoic acid | X |
| 60 | 2-Furoic acid | X |
| 61 | Indole-3-acetic acid | X |
| 62 | Tert-butylacetic acid | X |
| 63 | 3,3-diphenylpropionic acid | X |
| 64 | 5-Methyl-2-pyrazinecarboxylic acid | X |
| 65 | 2-Benzimidazolepropionic acid | X |
| 66 | 4-Phenylbutyric acid | X |
| 67 | 5-Bromo-2-furoic acid | X |
| 68 | 3-Bromopropionic acid | X |
| 69 | 3,3,3-triphenylpropionic acid | X |
| 70 | Myristic Acid | X |
| 71 | 2-chloropyrimidine | X |
| 72 | 2-Naphthoxyacetic acid | X |
| 73 | 2-Phenyl-4-quinolinecarboxylic acid | X |
| 74 | 3-(3,4,5-trimethoxyphenyl)-Propionic acid | X |
| 75 | 3,4-(methylenedioxy)-phenylacetic acid | X |
| 76 | 1-Methyl-2-pyrrolecarboxylic acid | X |
| 77 | 1-phenyl-1-cyclopentanecarboxylic acid | X |
| 78 | 2,3,4,5,6-pentafluorophenylacetic acid | X |
| 79 | 3,5-Bis(Trifluoromethyl)-benzoic acid | X |
| 80 | 4,5-dibromo-1H-pyrrole-2-carboxylic acid | X |
| 81 | 4-isopropylbenzoic acid | X |
| 82 | 5-methyl-3-phenylisoxazole-4-carboxylic acid | X |
| 83 | 2-methyl-4-nitro-1-imidazole-propionic acid | X |
| 84 | 2-Methylcyclopropanecarboxylic Acid | X |
| 85 | 3,3-Dimethylacrylic Acid | X |
| 86 | Dicyclohexylacetic Acid | X |
| 87 | Tert-Butylacetic Acid | X |
| 88 | Trans-3-Hexenoic Acid | X |
| 89 | 2-Napthylacetic acid | X |
| 90 | 3,4,5-Triethoxybenzoic acid | X |
| 91 | Diphenylacetic acid | X |
| 92 | 2-pyrazinecarboxylic acid | X |
| 93 | (Phenylthio) Acetic Acid | X |
| 94 | 2,4-Dichlorobenzoic acid | X |
| 95 | 2,4-DimethoxyBenzoic acid | X |
| 96 | 3,4-Dimethoxybenzoic acid | X |
| 97 | 3,5-Dimethylbenzoic acid | X |
| 98 | 3-Benzoylpropionic acid | X |
| 99 | 2-Cyclopentene-1-Acetic Acid | X |
| 100 | 4-Methylcyclohexaneacetic Acid | X |
| 101 | 4-tert-Butyl-Cyclohexanecarboxylic Acid | X |
| 102 | X | 1-phenyl-1-cyclopropanecarboxylic acid |
| 103 | X | 2-Phenylbutyric Acid |
| 104 | X | 3-Phenylbutyric Acid |
| 105 | X | m-Tolylacetic acid |
| 106 | X | 3-Fluorophenylacetic Acid |
| 107 | X | 3-Bromophenylacetic Acid |
| 108 | X | p-Tolyacetic acid |
| 109 | X | 4-Fluorophenylacetic acid |
| 110 | X | 3-Methoxyphenylacetic acid |
| 111 | X | 4-Bromophenylacetic acid |
| 112 | X | 4-Methoxyphenylacetic acid |
| 113 | X | 3,4-Dimethoxyphenylacetic acid |
| 114 | X | 4-isobutyl-alpha-Methylphenylacetic Acid |
| 115 | X | 3,4-Dichlorophenylacetic acid |
| 116 | X | 3,5-Bis(Trifluoromethyl)-Phenylacetic acid |
| 117 | X | 3-(3,4-Dimethoxyphenyl)-propionic Acid |
| 118 | X | Phenylacetic acid |
| 119 | X | 3,4,5-Trimethoxybenzoic acid |
| 120 | X | Butyric Acid |
| 121 | X | Heptanoic Acid |
| 122 | X | Isobutyric Acid |
| 123 | X | 2-Methylbutiric Acid |
| 124 | X | Isovaleric acid |
| 125 | X | 3-Methylvaleric acid |

TABLE 1-continued

Examples of compounds of Formula 1 tested

| # | R1 | R2 |
|---|---|---|
| 126 | X | p-Toluic Acid |
| 127 | X | cyclopentanecarboxylic acid. |
| 128 | X | cyclohexanecarboxilic acid |
| 129 | X | cyclohexylacetic acid |
| 130 | X | cyclohexanebutyric acid |
| 131 | X | cycloheptanecarboxylic acid |
| 132 | X | 1-Adamantaneacetic Acid |
| 133 | X | cyclobutanecarboxylic acid |
| 134 | X | 3-cyclopentylpropionic acid |
| 135 | X | cyclohexanepropionic acid |
| 136 | X | 4-methyl-1-cyclohexancarboxylic acid |
| 137 | X | 4-tert-butyl-cyclohexancecarboxylic acid |
| 138 | X | 4-biphenylacetic acid |
| 139 | X | 1-Adamantancecarboxylic acid |
| 140 | X | 4-Methylvaleric acid |
| 141 | X | 2-norbornaneacetic acid |
| 142 | X | Hexanoic Acid |
| 143 | X | Octanoic Acid |
| 144 | X | 2-Ethylbutyric Acid |
| 145 | X | Trimethylacetic Acid |
| 146 | X | Cyclopentylacetic Acid |
| 147 | X | 3-Cyclopentylpropionic Acid |
| 148 | X | 2-ethylhexanoic |
| 149 | X | 2-Phenoxypropionic acid |
| 150 | X | Benzoic acid |
| 151 | X | 2-Chlorobenzoic acid |
| 152 | X | 2-(P-Toluoyl)-Benzoic acid |
| 153 | X | m-Toluic acid |
| 154 | X | 4-Fluorobenzoic Acid |
| 155 | X | 4-Bromobenzoic Acid |
| 156 | X | 4-Ethylbiphenyl-4'-carboxylic acid |
| 157 | X | 3,4-Dimethylbenzoic acid |
| 158 | X | 4-Biphenylcarboxylic Acid |
| 159 | X | 2-BenzoylBenzoic acid |
| 160 | X | 1-Naphthoic acid |
| 161 | X | 2-Furoic acid |
| 162 | X | Indole-3-acetic acid |
| 163 | X | Tert-butylacetic acid |
| 164 | X | 3,3-diphenylpropionic acid |
| 165 | X | 5-Methyl-2-pyrazinecarboxylic acid |
| 166 | X | 2-Benzimidazolepropionic acid |
| 167 | X | 4-Phenylbutyric acid |
| 168 | X | 5-Bromo-2-furoic acid |
| 169 | X | 3-Bromopropionic acid |
| 170 | X | 3,3,3-triphenylpropionic acid |
| 171 | X | Myristic Acid |
| 172 | X | 2-chloropyrimidine |
| 173 | X | 2-Naphthoxyacetic acid |
| 174 | X | 2-Phenyl-4-quinolinecarboxylic acid |
| 175 | X | 3-(3,4,5-trimethoxyphenyl)-Propionic acid |
| 176 | X | 3,4-(methylenedioxy)-phenylacetic acid |
| 177 | X | 1-Methyl-2-pyrrolecarboxylic acid |
| 178 | X | 1-phenyl-1-cyclopentanecarboxylic acid |
| 179 | X | 2,3,4,5,6-pentafluorophenylacetic acid |
| 180 | X | 3,5-Bis(Trifluoromethyl)-benzoic acid |
| 181 | X | 4,5-dibromo-1H-pyrrole-2-carboxylic acid |
| 182 | X | 4-isopropylbenzoic acid |
| 183 | X | 5-methyl-3-phenylisoxazole-4-carboxylic acid |
| 184 | X | 2-methyl-4-nitro-1-imidazole-propionic acid |
| 185 | X | 2-Methylcyclopropanecarboxylic Acid |
| 186 | X | 3,3-Dimethylacrylic Acid |
| 187 | X | Dicyclohexylacetic Acid |
| 188 | X | Tert-Butylacetic Acid |
| 189 | X | Trans-3-Hexenoic Acid |
| 190 | X | 2-Napthylacetic acid |
| 191 | X | 3,4,5-Triethoxybenzoic acid |
| 192 | X | Diphenylacetic acid |
| 193 | X | 2-pyrazinecarboxylic acid |
| 194 | X | (Phenylthio) Acetic Acid |
| 195 | X | 2,4-Dichlorobenzoic acid |
| 196 | X | 2,4-DimethoxyBenzoic acid |
| 197 | X | 3,4-Dimethoxybenzoic acid |
| 198 | X | 3,5-Dimethylbenzoic acid |
| 199 | X | 3-Benzoylpropionic acid |
| 200 | X | 2-Cyclopentene-1-Acetic Acid |

TABLE 1-continued

Examples of compounds of Formula 1 tested

| # | R1 | R2 |
|---|---|---|
| 201 | X | 4-Methylcyclohexaneacetic Acid |
| 202 | X | 4-tert-Butyl-Cyclohexanecarboxylic Acid |

Individual Controls

| # | R1 | R2 |
|---|---|---|
| 216 | 1-phenyl-1-cyclopropanecarboxylic acid | Phenylacetic acid |
| 217 | 2-Phenylbutyric Acid | Phenylacetic acid |
| 218 | 3-Phenylbutyric Acid | Phenylacetic acid |
| 219 | m-Tolylacetic acid | Phenylacetic acid |
| 220 | 3-Fluorophenylacetic Acid | Phenylacetic acid |
| 221 | 3-Bromophenylacetic Acid | Phenylacetic acid |
| 222 | p-Tolyacetic acid | Phenylacetic acid |
| 223 | 4-Fluorophenylacetic acid | Phenylacetic acid |
| 224 | 3-Methoxyphenylacetic acid | Phenylacetic acid |
| 225 | 4-Bromophenylacetic acid | Phenylacetic acid |
| 226 | 4-Methoxyphenylacetic acid | Phenylacetic acid |
| 227 | 3,4-Dimethoxyphenylacetic acid | Phenylacetic acid |
| 228 | 4-isobutyl-alpha-Methylphenylacetic Acid | Phenylacetic acid |
| 229 | 3,4-Dichlorophenylacetic acid | Phenylacetic acid |
| 230 | 3,5-Bis(Trifluoromethyl)-Phenylacetic acid | Phenylacetic acid |
| 231 | 3-(3,4-Dimethoxyphenyl)-propionic Acid | Phenylacetic acid |
| 232 | Phenylacetic acid | Phenylacetic acid |
| 233 | 3,4,5-Trimethoxybenzoic acid | Phenylacetic acid |
| 234 | Butyric Acid | Phenylacetic acid |
| 235 | Heptanoic Acid | Phenylacetic acid |
| 236 | Isobutyric Acid | Phenylacetic acid |
| 237 | 2-Methylbutiric Acid | Phenylacetic acid |
| 238 | Isovaleric acid | Phenylacetic acid |
| 239 | 3-Methylvaleric acid | Phenylacetic acid |
| 240 | p-Toluic Acid | Phenylacetic acid |
| 241 | cyclopentanecarboxylic acid. | Phenylacetic acid |
| 242 | cyclohexanecarboxilic acid | Phenylacetic acid |
| 243 | cyclohexylacetic acid | Phenylacetic acid |
| 244 | cyclohexanebutyric acid | Phenylacetic acid |
| 245 | cycloheptanecarboxylic acid | Phenylacetic acid |
| 246 | 1-Adamantaneacetic Acid | Phenylacetic acid |
| 247 | cyclobutanecarboxylic acid | Phenylacetic acid |
| 248 | 3-cyclopentylpropionic acid | Phenylacetic acid |
| 249 | cyclohexanepropionic acid | Phenylacetic acid |
| 250 | 4-methyl-1-cyclohexancarboxylic acid | Phenylacetic acid |
| 251 | 4-tert-butyl-cyclohexanececarboxylic acid | Phenylacetic acid |
| 252 | 4-biphenylacetic acid | Phenylacetic acid |
| 253 | 1-Adamantancecarboxylic acid | Phenylacetic acid |
| 254 | 4-Methylvaleric acid | Phenylacetic acid |
| 255 | 2-norbornaneacetic acid | Phenylacetic acid |
| 256 | Hexanoic Acid | Phenylacetic acid |
| 257 | Octanoic Acid | Phenylacetic acid |
| 258 | 2-Ethylbutyric Acid | Phenylacetic acid |
| 259 | Trimethylacetic Acid | Phenylacetic acid |
| 260 | Cyclopentylacetic Acid | Phenylacetic acid |
| 261 | 3-Cyclopentylpropionic Acid | Phenylacetic acid |
| 262 | 2-ethylhexanoic | Phenylacetic acid |
| 263 | 2-Phenoxypropionic acid | Phenylacetic acid |
| 264 | Benzoic acid | Phenylacetic acid |
| 265 | 2-Chlorobenzoic acid | Phenylacetic acid |
| 266 | 2-(P-Toluoyl)-Benzoic acid | Phenylacetic acid |
| 267 | m-Toluic acid | Phenylacetic acid |
| 268 | 4-Fluorobenzoic Acid | Phenylacetic acid |
| 269 | 4-Bromobenzoic Acid | Phenylacetic acid |
| 270 | 4-Ethylbiphenyl-4'-carboxylic acid | Phenylacetic acid |
| 271 | 3,4-Dimethylbenzoic acid | Phenylacetic acid |
| 272 | 4-Biphenylcarboxylic Acid | Phenylacetic acid |
| 273 | 2-BenzoylBenzoic acid | Phenylacetic acid |
| 274 | 1-Naphthoic acid | Phenylacetic acid |
| 275 | 2-Furoic acid | Phenylacetic acid |
| 276 | Indole-3-acetic acid | Phenylacetic acid |
| 277 | Tert-butylacetic acid | Phenylacetic acid |
| 278 | 3,3-diphenylpropionic acid | Phenylacetic acid |
| 279 | 5-Methyl-2-pyrazinecarboxylic acid | Phenylacetic acid |
| 280 | 2-Benzimidazolepropionic acid | Phenylacetic acid |
| 281 | 4-Phenylbutyric acid | Phenylacetic acid |
| 282 | 5-Bromo-2-furoic acid | Phenylacetic acid |
| 283 | 3-Bromopropionic acid | Phenylacetic acid |
| 284 | 3,3,3-triphenylpropionic acid | Phenylacetic acid |
| 285 | Myristic Acid | Phenylacetic acid |
| 286 | 2-chloropyrimidine | Phenylacetic acid |
| 287 | 2-Naphthoxyacetic acid | Phenylacetic acid |

TABLE 1-continued

Examples of compounds of Formula 1 tested

| # | R1 | R2 |
|---|----|----|
| 288 | 2-Phenyl-4-quinolinecarboxylic acid | Phenylacetic acid |
| 289 | 3-(3,4,5-trimethoxyphenyl)-Propionic acid | Phenylacetic acid |
| 290 | 3,4-(methylenedioxy)-phenylacetic acid | Phenylacetic acid |
| 291 | 1-Methyl-2-pyrrolecarboxylic acid | Phenylacetic acid |
| 292 | 1-phenyl-1-cyclopentanecarboxylic acid | Phenylacetic acid |
| 293 | 2,3,4,5,6-pentafluorophenylacetic acid | Phenylacetic acid |
| 294 | 3,5-Bis(Trifluoromethyl)-benzoic acid | Phenylacetic acid |
| 295 | 4,5-dibromo-1H-pyrrole-2-carboxylic acid | Phenylacetic acid |
| 296 | 4-isopropylbenzoic acid | Phenylacetic acid |
| 297 | 5-methyl-3-phenylisoxazole-4-carboxylic acid | Phenylacetic acid |
| 298 | 2-methyl-4-nitro-1-imidazole-propionic acid | Phenylacetic acid |
| 299 | 2-Methylcyclopropanecarboxylic Acid | Phenylacetic acid |
| 300 | 3,3-Dimethylacrylic Acid | Phenylacetic acid |
| 301 | Dicyclohexylacetic Acid | Phenylacetic acid |
| 302 | Tert-Butylacetic Acid | Phenylacetic acid |
| 303 | Trans-3-Hexenoic Acid | Phenylacetic acid |
| 304 | 2-Napthylacetic acid | Phenylacetic acid |
| 305 | 3,4,5-Triethoxybenzoic acid | Phenylacetic acid |
| 306 | Diphenylacetic acid | Phenylacetic acid |
| 307 | 2-pyrazinecarboxylic acid | Phenylacetic acid |
| 308 | (Phenylthio) Acetic Acid | Phenylacetic acid |
| 309 | 2,4-Dichlorobenzoic acid | Phenylacetic acid |
| 310 | 2,4-DimethoxyBenzoic acid | Phenylacetic acid |
| 311 | 3,4-Dimethoxybenzoic acid | Phenylacetic acid |
| 312 | 3,5-Dimethylbenzoic acid | Phenylacetic acid |
| 313 | 3-Benzoylpropionic acid | Phenylacetic acid |
| 314 | 2-Cyclopentene-1-Acetic Acid | Phenylacetic acid |
| 315 | 4-Methylcyclohexaneacetic Acid | Phenylacetic acid |
| 316 | 4-tert-Butyl-Cyclohexanecarboxylic Acid | Phenylacetic acid |
| 317 | Phenylacetic acid | 1-phenyl-1-cyclopropanecarboxylic acid |
| 318 | Phenylacetic acid | 2-Phenylbutyric Acid |
| 319 | Phenylacetic acid | 3-Phenylbutyric Acid |
| 320 | Phenylacetic acid | m-Tolylacetic acid |
| 321 | Phenylacetic acid | 3-Fluorophenylacetic Acid |
| 322 | Phenylacetic acid | 3-Bromophenylacetic Acid |
| 323 | Phenylacetic acid | p-Tolyacetic acid |
| 324 | Phenylacetic acid | 4-Fluorophenylacetic acid |
| 325 | Phenylacetic acid | 3-Methoxyphenylacetic acid |
| 326 | Phenylacetic acid | 4-Bromophenylacetic acid |
| 327 | Phenylacetic acid | 4-Methoxyphenylacetic acid |
| 328 | Phenylacetic acid | 3,4-Dimethoxyphenylacetic acid |
| 329 | Phenylacetic acid | 4-isobutyl-alpha-Methylphenylacetic Acid |
| 330 | Phenylacetic acid | 3,4-Dichlorophenylacetic acid |
| 331 | Phenylacetic acid | 3,5-Bis(Trifluoromethyl)-Phenylacetic acid |
| 332 | Phenylacetic acid | 3-(3,4-Dimethoxyphenyl)-propionic Acid |
| 333 | Phenylacetic acid | Phenylacetic acid |
| 334 | Phenylacetic acid | 3,4,5-Trimethoxybenzoic acid |
| 335 | Phenylacetic acid | Butyric Acid |
| 336 | Phenylacetic acid | Heptanoic Acid |
| 337 | Phenylacetic acid | Isobutyric Acid |
| 338 | Phenylacetic acid | 2-Methylbutiric Acid |
| 339 | Phenylacetic acid | Isovaleric acid |
| 340 | Phenylacetic acid | 3-Methylvaleric acid |
| 341 | Phenylacetic acid | p-Toluic Acid |
| 342 | Phenylacetic acid | cyclopentanecarboxylic acid. |
| 343 | Phenylacetic acid | cyclohexanecarboxilic acid |
| 344 | Phenylacetic acid | cyclohexylacetic acid |
| 345 | Phenylacetic acid | cyclohexanebutyric acid |
| 346 | Phenylacetic acid | cycloheptanecarboxylic acid |
| 347 | Phenylacetic acid | 1-Adamantaneacetic Acid |
| 348 | Phenylacetic acid | cyclobutanecarboxylic acid |
| 349 | Phenylacetic acid | 3-cyclopentylpropionic acid |
| 350 | Phenylacetic acid | cyclohexanepropionic acid |
| 351 | Phenylacetic acid | 4-methyl-1-cyclohexancarboxylic acid |
| 352 | Phenylacetic acid | 4-tert-butyl-cyclohexancecarboxylic acid |
| 353 | Phenylacetic acid | 4-biphenylacetic acid |
| 354 | Phenylacetic acid | 1-Adamantancecarboxylic acid |
| 355 | Phenylacetic acid | 4-Methylvaleric acid |
| 356 | Phenylacetic acid | 2-norbornaneacetic acid |
| 357 | Phenylacetic acid | Hexanoic Acid |
| 358 | Phenylacetic acid | Octanoic Acid |
| 359 | Phenylacetic acid | 2-Ethylbutyric Acid |
| 360 | Phenylacetic acid | Trimethylacetic Acid |
| 361 | Phenylacetic acid | Cyclopentylacetic Acid |
| 362 | Phenylacetic acid | 3-Cyclopentylpropionic Acid |
| 363 | Phenylacetic acid | 2-ethylhexanoic |

TABLE 1-continued

Examples of compounds of Formula 1 tested

| # | R1 | R2 |
|---|---|---|
| 364 | Phenylacetic acid | 2-Phenoxypropionic acid |
| 365 | Phenylacetic acid | Benzoic acid |
| 366 | Phenylacetic acid | 2-Chlorobenzoic acid |
| 367 | Phenylacetic acid | 2-(P-Toluoyl)-Benzoic acid |
| 368 | Phenylacetic acid | m-Toluic acid |
| 369 | Phenylacetic acid | 4-Fluorobenzoic Acid |
| 370 | Phenylacetic acid | 4-Bromobenzoic Acid |
| 371 | Phenylacetic acid | 4-Ethylbiphenyl-4'-carboxylic acid |
| 372 | Phenylacetic acid | 3,4-Dimethylbenzoic acid |
| 373 | Phenylacetic acid | 4-Biphenylcarboxylic Acid |
| 374 | Phenylacetic acid | 2-BenzoylBenzoic acid |
| 375 | Phenylacetic acid | 1-Naphthoic acid |
| 376 | Phenylacetic acid | 2-Furoic acid |
| 377 | Phenylacetic acid | Indole-3-acetic acid |
| 378 | Phenylacetic acid | Tert-butylacetic acid |
| 379 | Phenylacetic acid | 3,3-diphenylpropionic acid |
| 380 | Phenylacetic acid | 5-Methyl-2-pyrazinecarboxylic acid |
| 381 | Phenylacetic acid | 2-Benzimidazolepropionic acid |
| 382 | Phenylacetic acid | 4-Phenylbutyric acid |
| 383 | Phenylacetic acid | 5-Bromo-2-furoic acid |
| 384 | Phenylacetic acid | 3-Bromopropionic acid |
| 385 | Phenylacetic acid | 3,3,3-triphenylpropionic acid |
| 386 | Phenylacetic acid | Myristic Acid |
| 387 | Phenylacetic acid | 2-chloropyrimidine |
| 388 | Phenylacetic acid | 2-Naphthoxyacetic acid |
| 389 | Phenylacetic acid | 2-Phenyl-4-quinolinecarboxylic acid |
| 390 | Phenylacetic acid | 3-(3,4,5-trimethoxyphenyl)-Propionic acid |
| 391 | Phenylacetic acid | 3,4-(methylenedioxy)-phenylacetic acid |
| 392 | Phenylacetic acid | 1-Methyl-2-pyrrolecarboxylic acid |
| 393 | Phenylacetic acid | 1-phenyl-1-cyclopentanecarboxylic acid |
| 394 | Phenylacetic acid | 2,3,4,5,6-pentafluorophenylacetic acid |
| 395 | Phenylacetic acid | 3,5-Bis(Trifluoromethyl)-benzoic acid |
| 396 | Phenylacetic acid | 4,5-dibromo-1H-pyrrole-2-carboxylic acid |
| 397 | Phenylacetic acid | 4-isopropylbenzoic acid |
| 398 | Phenylacetic acid | 5-methyl-3-phenylisoxazole-4-carboxylic acid |
| 399 | Phenylacetic acid | 2-methyl-4-nitro-1-imidazole-propionic acid |
| 400 | Phenylacetic acid | 2-Methylcyclopropanecarboxylic Acid |
| 401 | Phenylacetic acid | 3,3-Dimethylacrylic Acid |
| 402 | Phenylacetic acid | Dicyclohexylacetic Acid |
| 403 | Phenylacetic acid | Tert-Butylacetic Acid |
| 404 | Phenylacetic acid | Trans-3-Hexenoic Acid |
| 405 | Phenylacetic acid | 2-Napthylacetic acid |
| 406 | Phenylacetic acid | 3,4,5-Triethoxybenzoic acid |
| 407 | Phenylacetic acid | Diphenylacetic acid |
| 408 | Phenylacetic acid | 2-pyrazinecarboxylic acid |
| 409 | Phenylacetic acid | (Phenylthio) Acetic Acid |
| 410 | Phenylacetic acid | 2,4-Dichlorobenzoic acid |
| 411 | Phenylacetic acid | 2,4-DimethoxyBenzoic acid |
| 412 | Phenylacetic acid | 3,4-Dimethoxybenzoic acid |
| 413 | Phenylacetic acid | 3,5-Dimethylbenzoic acid |
| 414 | Phenylacetic acid | 3-Benzoylpropionic acid |
| 415 | Phenylacetic acid | 2-Cyclopentene-1-Acetic Acid |
| 416 | Phenylacetic acid | 4-Methylcyclohexaneacetic Acid |
| 417 | Phenylacetic acid | 4-tert-Butyl-Cyclohexanecarboxylic Acid |
| 418 | Phenylacetic acid | Phenylacetic acid |
| 419 | Phenylacetic acid | Phenylacetic acid |
| 420 | Phenylacetic acid | Phenylacetic acid |
| 421 | Phenylacetic acid | Phenylacetic acid |
| 422 | Phenylacetic acid | Phenylacetic acid |
| 423 | Phenylacetic acid | Phenylacetic acid |
| 424 | Phenylacetic acid | Phenylacetic acid |
| 425 | Phenylacetic acid | Phenylacetic acid |
| 426 | Phenylacetic acid | Phenylacetic acid |
| 427 | Phenylacetic acid | Phenylacetic acid |
| 428 | Phenylacetic acid | Phenylacetic acid |
| 429 | Phenylacetic acid | Phenylacetic acid |
| 430 | Phenylacetic acid | Phenylacetic acid |

That which is claimed is:
1. A composition comprising a pharmaceutical dosage form including a compound of the formula

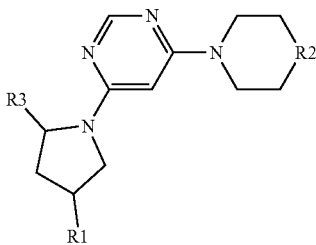

and/or a pharmaceutically effective salt thereof wherein:
(a) R1 is selected from 3-methylvaleramide, myristic amide, 2,4-dichlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide;
(b) R2 maintains the six-membered ring and is selected from:
  (i) an amide group, a thioamide group, a valeramide group, a myristic amide group, a benzamide group, a carboxylamide group, and a phenylacetamide group;
  (ii) O, S, CR4R5 where R4 and R5 are independently selected from a hydrogen, a halogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group; or
  (iii) N—R2' where R2' is selected from a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, and a thiourea group; and
(c) R3 is selected from:
  (i) a halogen, a hydrogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group; or
  (ii) OH, OR6, NH2, where R6 is selected from H, an aliphatic group, an alkylaryl group, a cycloalkyl group, an alkylcycloalkyl group, and an aryl group.
2. The composition of claim 1, wherein R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide.
3. The composition of claim 1, wherein R3 is an amide group.
4. The composition of claim 1, wherein:
R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide; and
R3 is an amide group.
5. The composition of claim 1, wherein the pharmaceutical dosage form is at least one of a pill or an injectable dosage form.
6. The composition of claim 1, wherein the compound is substantially non-toxic.
7. A method comprising administering to a patient having a fibrotic condition a therapeutically amount of the composition of claim 1 to the patient.
8. The method of claim 7, wherein R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide.
9. The method of claim 7, wherein R3 is an amide group.
10. The method of claim 7, wherein:
R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide; and
R3 is an amide group.
11. The method of claim 7, wherein the fibrotic condition is at least one of a pulmonary fibrosis, a liver fibrosis, a heart fibrosis, a circulatory system fibrosis, a skin fibrosis, and an intestinal fibrosis.
12. The method of claim 7, wherein administering is oral administration and/or administration by injection.
13. The method of claim 7, wherein the pharmaceutical dosage form is at least one of a pill or an injectable dosage form.
14. A method of inhibiting collagen production, the method comprising contacting a cell capable of producing type 1 collagen with the composition of claim 1, the composition being effective for inhibiting collagen production.
15. The method of claim 14, wherein R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide.
16. The method of claim 14, wherein R3 is an amide group.
17. The method of claim 14, wherein:
R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide; and
R3 is an amide group.

18. A composition comprising a pharmaceutical dosage form including a compound of the formula

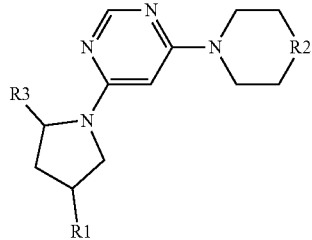

and/or a pharmaceutically effective salt thereof wherein:
(a) R1 is selected from a halogen, a hydrogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group;
(b) R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide; and
(c) R3 is selected from:
(i) a halogen, a hydrogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group; or
(ii) OH, OR6, $NH_2$, where R6 is selected from H, an aliphatic group, an alkylaryl group, a cycloalkyl group, an alkylcycloalkyl group, and an aryl group.

19. composition of claim 18, wherein R1 is selected from 3-methylvaleramide, myristic amide, 2,4-dichlorobenzamide, 2-(P-Toluoyl) -benzamide, 1-methyl-2-pyrrolecarboxylamide, 4-isobutyl-alpha -methylphenylacetamide, 4-bromobenzamide, pentafluorophenyacetamide, and phenylacetamide.

20. The composition of claim 18, wherein R3 is an amide group.

21. The composition of claim 18, wherein:
R1 is selected from 3-methylvaleramide, myristic amide, 2,4-dichlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide; and
R3 is an amide group.

22. The composition of claim 18, wherein the pharmaceutical dosage form is at least one of a pill or an injectable dosage form.

23. The composition of claim 18, wherein the compound is substantially non-toxic.

24. A method comprising administering to a patient having a fibrotic condition a therapeutically amount of the composition of claim 18 to the patient.

25. The method of claim 24, wherein R1 is selected from 3-methylvaleramide, myristic amide, 2,4-dichlorobenzamide, 2-(P-Toluoyl) -benzamide, 1-methyl-2-pyrrolecarboxylamide, 4-isobutyl-alpha -methylphenylacetamide, 4-bromobenzamide, pentafluorophenyacetamide, and phenylacetamide.

26. The method of claim 24, wherein R3 is an amide group.

27. The method of claim 24, wherein:
R1 is selected from 3-methylvaleramide, myristic amide, 2,4-dichlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide; and
R3 is an amide group.

28. The method of claim 24, wherein the fibrotic condition is at least one of a pulmonary fibrosis, a liver fibrosis, a heart fibrosis, a circulatory system fibrosis, a skin fibrosis, and an intestinal fibrosis.

29. The method of claim 24, wherein administering is oral administration and/or administration by injection.

30. The method of claim 24, wherein the pharmaceutical dosage form is at least one of a pill or an injectable dosage form.

31. A method of inhibiting collagen production, the method comprising contacting a cell capable of producing type 1 collagen with the composition of claim 18, the composition being effective for inhibiting collagen production.

32. The method of claim 31, wherein R1 is selected from 3-methylvaleramide, myristic amide, 2,4-dichlorobenzamide, 2-(P-Toluoyl) -benzamide, 1-methyl-2-pyrrolecarboxylamide, 4-isobutyl-alpha -methylphenylacetamide, 4-bromobenzamide, pentafluorophenyacetamide, and phenylacetamide.

33. The method of claim 31, wherein R3 is an amide group.

34. The method of claim 31, wherein:
R1 is selected from 3-methylvaleramide, myristic amide, 2,4-dichlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide; and
R3 is an amide group.

35. A composition comprising a pharmaceutical dosage form including a compound of the formula

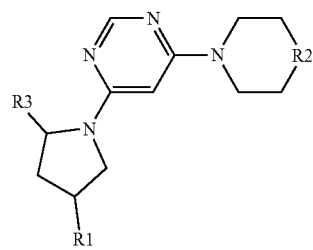

and/or a pharmaceutically effective salt thereof wherein:
R1 is selected from 3-methylvaleramide, myristic amide, 2,4-dichlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide; and
R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide; and R3 is an amide group.

36. The composition of claim 35, wherein the pharmaceutical dosage form is at least one of a pill or an injectable dosage form.

37. The composition of claim 35, wherein the compound is substantially non-toxic.

38. A method comprising administering to a patient having a fibrotic condition a therapeutically amount of the composition of claim 35 to the patient.

39. The method of claim 38, wherein the fibrotic condition is at least one of a pulmonary fibrosis, a liver fibrosis, a heart fibrosis, a circulatory system fibrosis, a skin fibrosis, and an intestinal fibrosis.

40. The method of claim 38, wherein administering is oral administration and/or administration by injection.

41. The method of claim 38, wherein the pharmaceutical dosage form is at least one of a pill or an injectable dosage form.

42. A method of inhibiting collagen production, the method comprising contacting a cell capable of producing type 1 collagen with the composition of claim 35, the composition being effective for inhibiting collagen production.

43. A method comprising administering to a patient having a fibrotic condition a therapeutically amount of a composition to the patient, the composition comprising a pharmaceutical dosage form including a compound of the formula

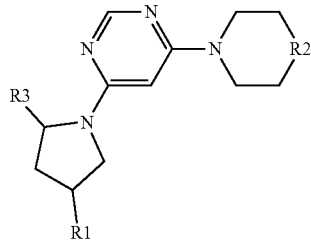

and/or a pharmaceutically effective salt thereof wherein:
(a) R1 is selected from a halogen, a hydrogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group;
(b) R2 maintains the six-membered ring and is selected from:
  (i) an amide group, a thioamide group, a valeramide group, a myristic amide group, a benzamide group, a carboxylamide group, and a phenylacetamide group;
  (ii) O, S, CR4R5 where R4 and R5 are independently selected from a hydrogen, a halogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group; or
  (iii) N—R2' where R2' is selected from a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, and a thiourea group; and
(c) R3 is an amide group.

44. The method of claim 43, wherein R1 is selected from 3-methylvaleramide, myristic amide, 2,4-dichlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide.

45. The method of claim 43, wherein R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dimethylbenzamide, phenylacetamide, 3,4,5-trimethoxybenzamide, 2-benzoylbenzamide, and myristic amide.

46. The method of claim 43, wherein:
R1 is selected from 3-methylvaleramide, myristic amide, 2,4-dichlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide; and
R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dinnethylbenzamide, phenylacetamide, 3,4,5-trimethoxybenzamide, 2-benzoylbenzamide, and myristic amide.

47. The method of claim 43, wherein the fibrotic condition is at least one of a pulmonary fibrosis, a liver fibrosis, a heart fibrosis, a circulatory system fibrosis, a skin fibrosis, and an intestinal fibrosis.

48. The method of claim 43, wherein administering is oral administration and/or administration by injection.

49. The method of claim 43, wherein the pharmaceutical dosage form is at least one of a pill or an injectable dosage form.

50. A method of inhibiting collagen production, the method comprising contacting a cell capable of producing type 1 collagen with a composition effective for inhibiting collagen production, the composition comprising a pharmaceutical dosage form including a compound of the formula

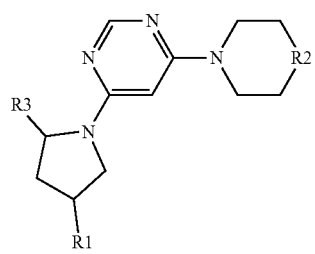

and/or a pharmaceutically effective salt thereof wherein:
(a) R1 is selected from a halogen, a hydrogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group;
(b) R2 maintains the six-membered ring and is selected from:
  (i) an amide group, a thioamide group, a valeramide group, a myristic amide group, a benzamide group, a carboxylamide group, and a phenylacetamide group;
  (ii) O, S, CR4R5 where R4 and R5 are independently selected from a hydrogen, a halogen, a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, a thiourea group, a valeramide group, a myristic amide group, a benzamide group, a carboxylamide group, and a phenylacetamide group; or
  (iii) N—R2' where R2' is selected from a saturated or unsaturated alkyl group, a saturated or unsaturated cycloalkyl group, an aryl group, an alkoxy group, a hydroxy group, a carboxy group, a carbonyl group, an amine group, an amide group, an ester group, a haloalkyl group, a haloaryl group, a thio group, a thioamide group, a urea group, and a thiourea group; and
(c) R3 is an amide group.

51. The method of claim 50, wherein R1 is selected from 3-methylvaleramide, myristic amide, 2,4-dichlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide.

52. The method of claim 50, wherein R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dinnethylbenzamide, phenylacetamide, 3,4,5-trimethoxybenzamide, 2-benzoylbenzamide, and myristic amide.

53. The method of claim 50, wherein:
R1 is selected from 3-methylvaleramide, myristic amide, 2,4-dichlorobenzamide, 2-(P-Toluoyl)-benzamide, 1-methyl-2-pyrrolecarboxylamide, 4-isobutyl-alpha-methylphenylacetamide, 4-bromobenzamide, pentafluorophenyacetamide, and phenylacetamide; and
R2 is selected from 3,4-dichlorophenylacetamide, 2-ethylbutyramide, 4-phenylbutyramide, 1-phenyl-1-cyclopentane carboxylamide, 2,4-dichlorobenzamide, 3,5-dinnethylbenzamide, phenylacetamide, 3,4,5-trimethoxybenzamide, 2-benzoylbenzamide, and myristic amide.

* * * * *